United States Patent
Haque et al.

(10) Patent No.: US 7,357,027 B2
(45) Date of Patent: Apr. 15, 2008

(54) ULTRASONIC SENSOR SYSTEM FOR WEB-GUIDING APPARATUS

(75) Inventors: Md M. Haque, Edmond, OK (US); Jim Yates, Edmond, OK (US); Wolfram Ploetz, Edmond, OK (US); Darcy J. Winter, Oklahoma City, OK (US); Dale Hueppelsheuser, Jones, OK (US)

(73) Assignee: Fife Corporation, Oklahoma City, OK (US)

( * ) Notice: Subject to any disclaimer, the term of this patent is extended or adjusted under 35 U.S.C. 154(b) by 0 days.

(21) Appl. No.: 11/483,203

(22) Filed: Jul. 7, 2006

(65) Prior Publication Data

US 2006/0254360 A1    Nov. 16, 2006

Related U.S. Application Data

(62) Division of application No. 10/922,019, filed on Aug. 19, 2004.

(51) Int. Cl.
*G01N 29/24* (2006.01)

(52) U.S. Cl. .............................. 73/597; 73/599; 73/159; 73/628

(58) Field of Classification Search ................. 73/159, 73/597–600, 628–629
See application file for complete search history.

(56) References Cited

U.S. PATENT DOCUMENTS

| | | | |
|---|---|---|---|
| 3,928,777 A | 12/1975 | Massa | |
| 4,329,838 A | 5/1982 | Zerle et al. | |
| 4,330,909 A | 5/1982 | Peschke et al. | |
| 4,366,406 A | 12/1982 | Smith et al. | |
| 4,523,122 A | 6/1985 | Tone et al. | |
| 4,532,167 A | 7/1985 | Mohr | |
| 4,606,486 A | 8/1986 | Brunner et al. | |
| 4,727,260 A | 2/1988 | Krauth | |
| 4,760,626 A | 8/1988 | Lonner et al. | |
| 4,780,631 A | 10/1988 | Groninger | |
| 4,848,632 A | 7/1989 | Mack et al. | |
| 4,920,622 A | 5/1990 | Mair et al. | |

(Continued)

*Primary Examiner*—Hezron Williams
*Assistant Examiner*—Nashmiya Fayyaz
(74) *Attorney, Agent, or Firm*—Dunlap Codding & Rogers, P.C.

(57) ABSTRACT

A sensor system for determining the position of at least one edge of at least one web material traveling along a predetermined path. In one embodiment, the sensor system has at least one transmitter block having a plurality of transmitters capable of selectively transmitting ultrasonic signals and at least one receiver block having a plurality of receivers capable of generating receiver output signals in response to the receivers receiving at least a portion of the ultrasonic signals transmitted by the at least one transmitter block. The receiver block is spaced a distance from the transmitter block so as to define a sensor field of view therebetween whereby at least a portion of the at least one web material traveling along a predetermined travel path interferes with at least a portion of the ultrasonic signals transmitted by the at least one transmitter block. The receiver output signals generated by the at least one receiver block is indicative of the position of the web of material as the same is moved along the travel path between the transmitter block and the receiver block. In an alternative embodiment, the functions of the at least one transmitter block and the at least one receiver block are performed essentially equivalently by at least one transceiver block and at least one reflector.

12 Claims, 26 Drawing Sheets

U.S. PATENT DOCUMENTS

| | | |
|---|---|---|
| 5,021,674 A | 6/1991 | Brunner |
| 5,036,706 A * | 8/1991 | Gnuechtel et al. ............ 73/597 |
| 5,072,414 A | 12/1991 | Buisker et al. |
| 5,133,511 A | 7/1992 | Mack et al. |
| 5,166,532 A | 11/1992 | Brunner et al. |
| 5,274,573 A | 12/1993 | Buisker et al. |
| 5,307,973 A | 5/1994 | Schmidt et al. |
| 5,322,990 A | 6/1994 | Brau et al. |
| 5,377,891 A | 1/1995 | Peltzer et al. |
| 5,421,500 A | 6/1995 | Niemann et al. |
| 5,565,627 A * | 10/1996 | Dorr ........................... 73/599 |
| 5,575,414 A | 11/1996 | Groninger et al. |
| 5,619,779 A | 4/1997 | Geyer |
| 5,663,510 A | 9/1997 | Niemann et al. |
| 5,803,334 A | 9/1998 | Patel et al. |
| 5,834,877 A | 11/1998 | Buisker et al. |
| 5,921,452 A | 7/1999 | Wulf et al. |
| 6,289,729 B1 | 9/2001 | Haque et al. |
| 6,323,948 B2 | 11/2001 | Haque et al. |
| 6,348,696 B1 | 2/2002 | Alt et al. |
| 6,450,381 B1 | 9/2002 | Ernst et al. |
| 6,474,528 B2 | 11/2002 | Scharschinger et al. |
| 6,550,656 B2 | 4/2003 | Kurz |
| 6,566,670 B1 | 5/2003 | Buisker et al. |
| 6,717,168 B2 | 4/2004 | Eisen et al. |
| 6,757,064 B2 | 6/2004 | Eisen et al. |
| 7,151,715 B2 * | 12/2006 | Eisen et al. ................. 367/129 |

* cited by examiner

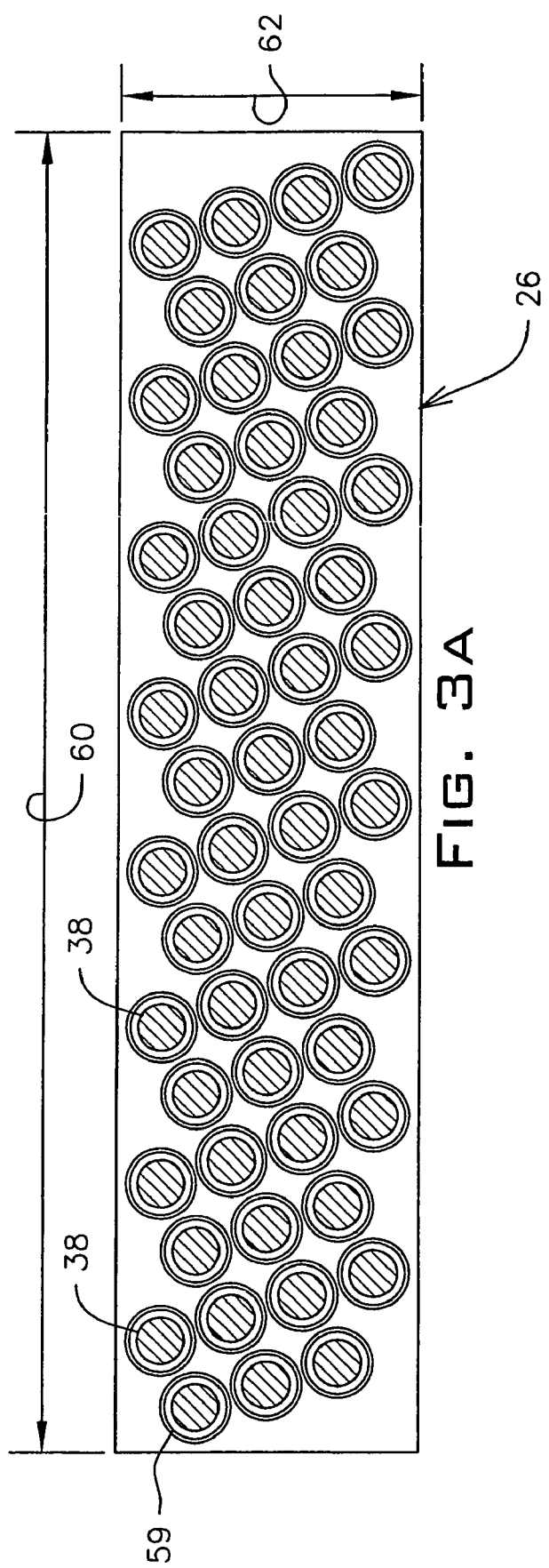

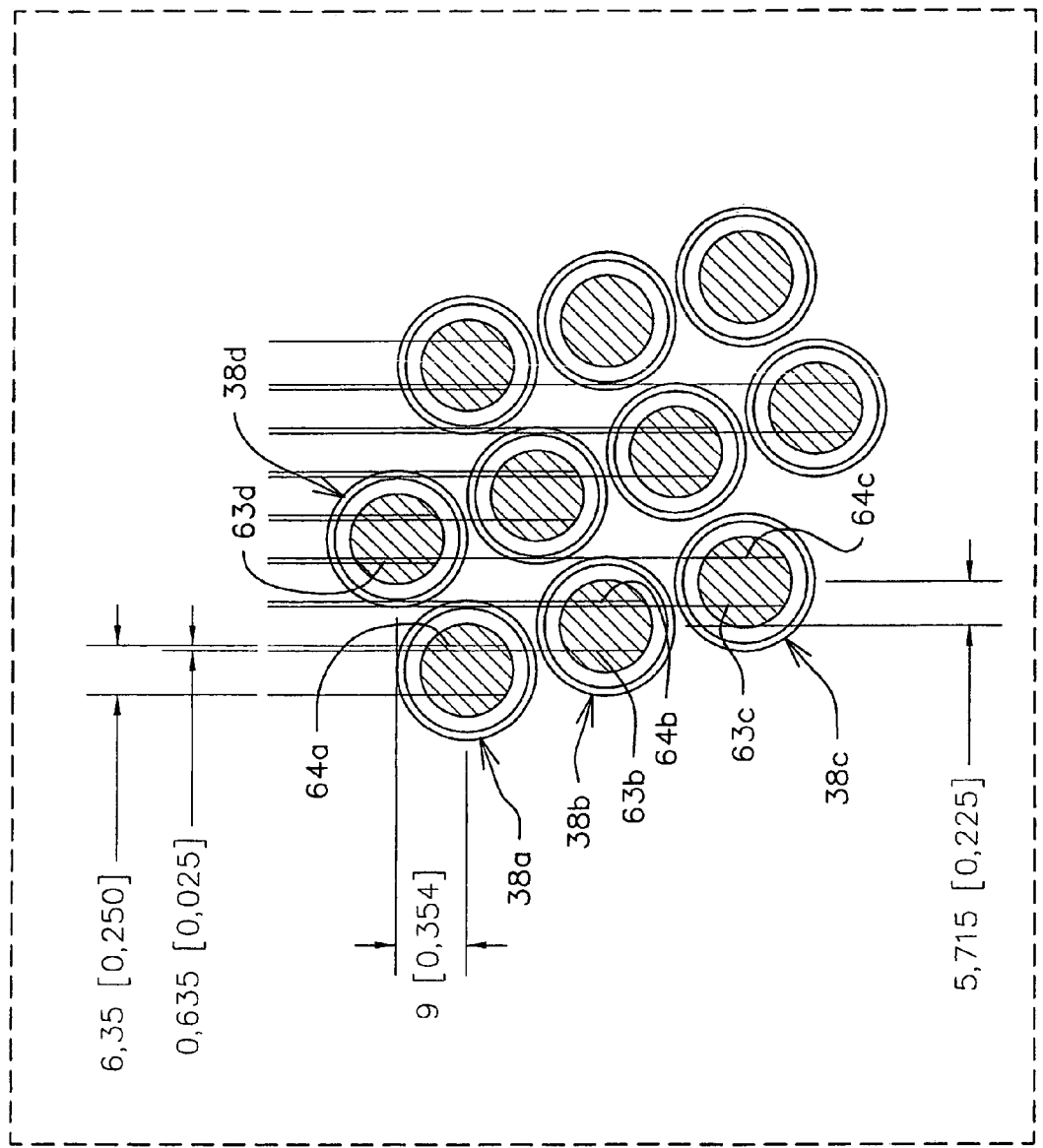

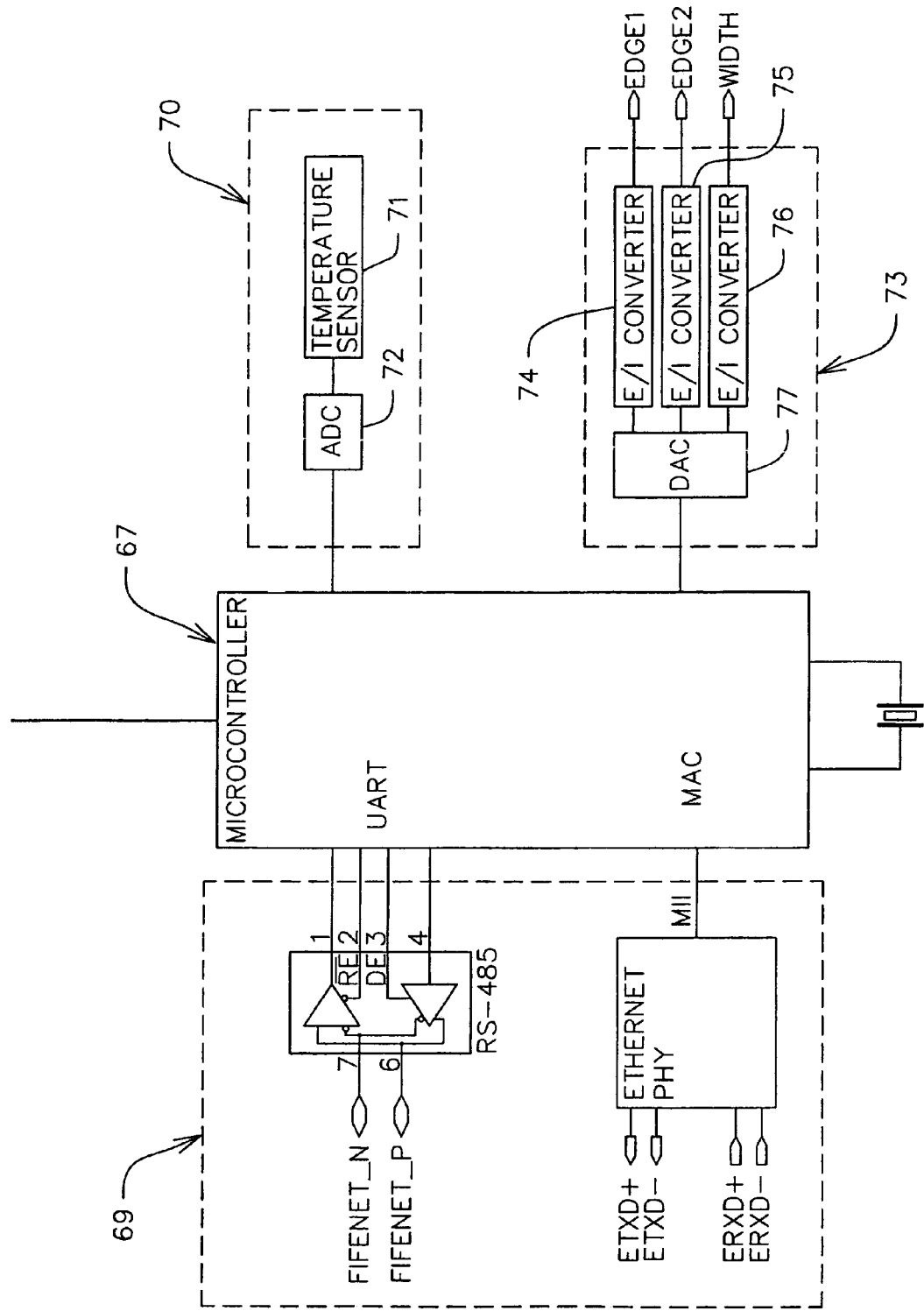

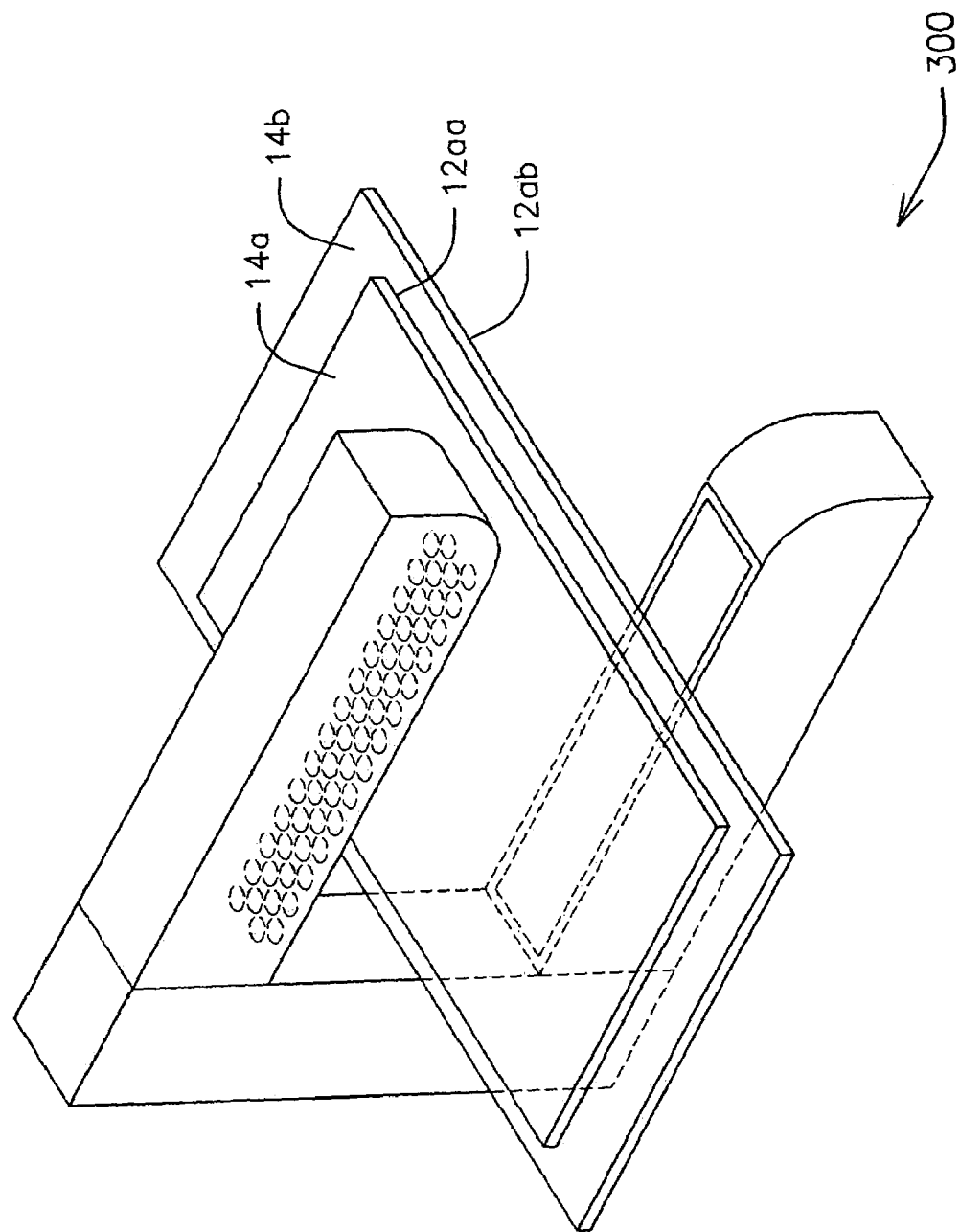

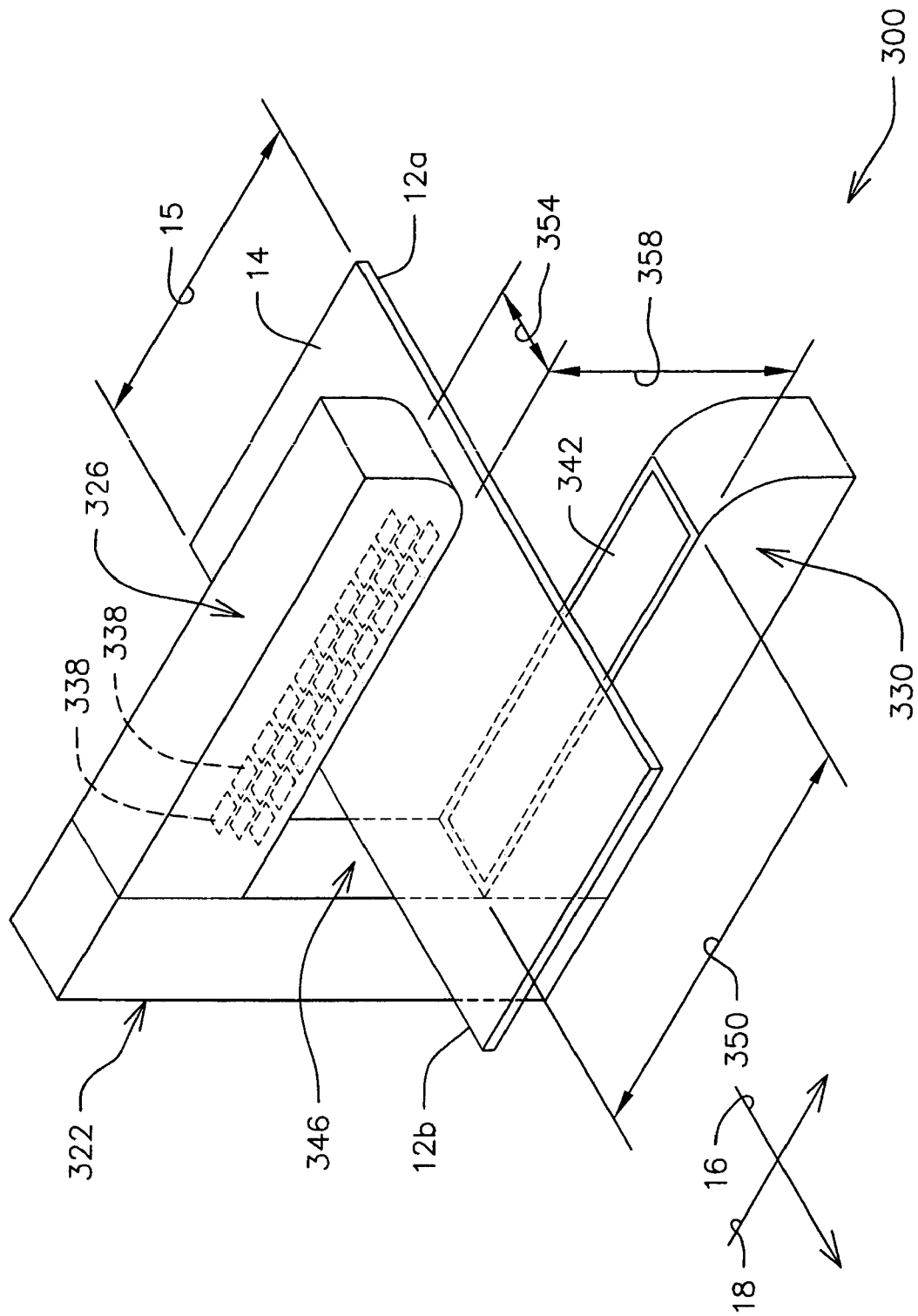

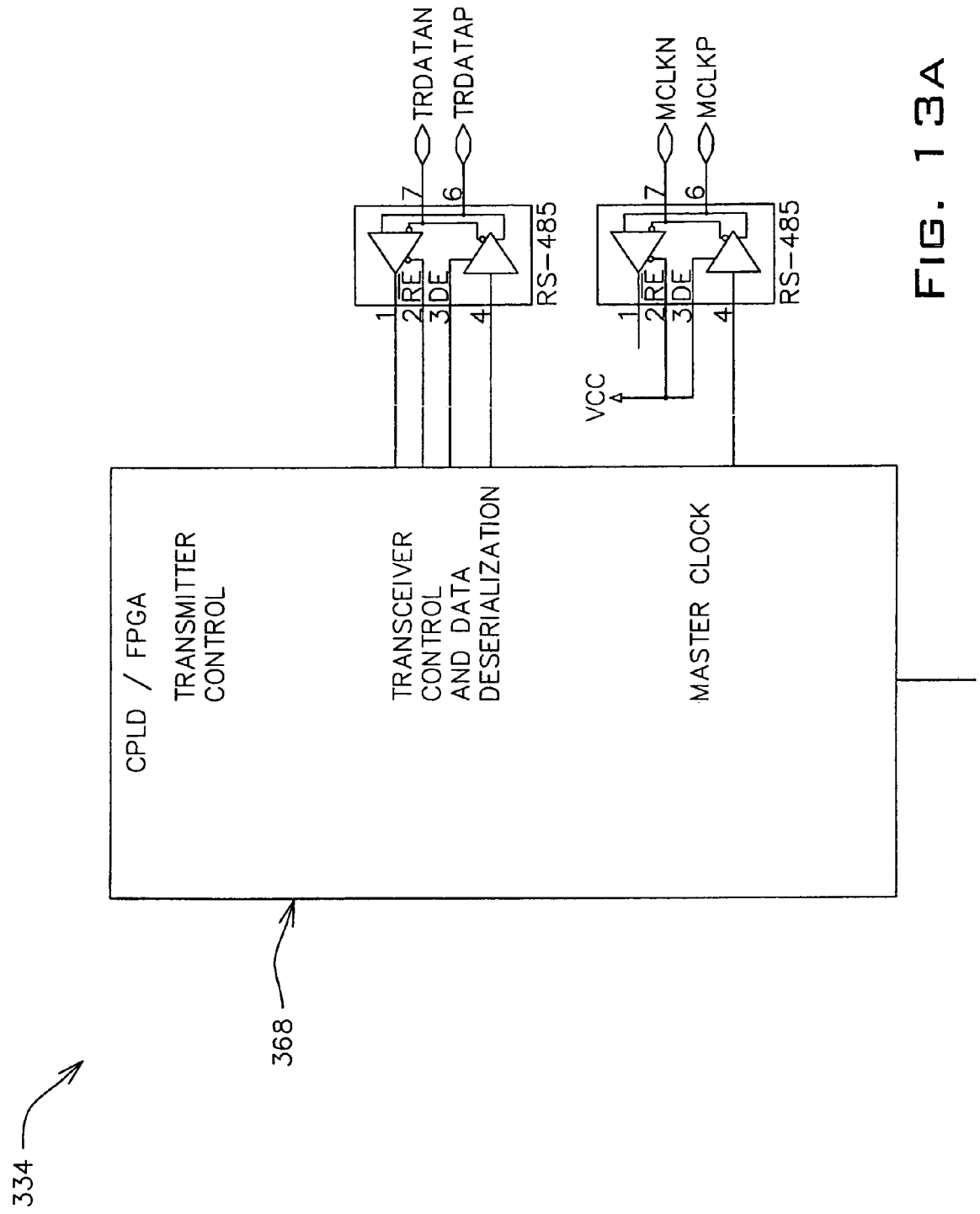

ULTRASONIC SENSOR SYSTEM FOR WEB-GUIDING APPARATUS

CROSS-REFERENCE TO RELATED APPLICATIONS

This application is a divisional of Ser. No. 10/922,019, filed on Aug. 19, 2004.

BACKGROUND OF THE INVENTION

Ultrasonic sensors having a transmitter disposed on one side of a web material and a receiver disposed on the other side of the web material for locating the position of an edge of the web material therebetween, are known in the art. Such ultrasonic sensors are mounted perpendicular to the web material direction of travel and suffer from problems due to the reflection of sound between the transmitter, the web material, and the receiver. Noise is thereby introduced into the signal produced by the receiver, and reduces the accuracy of the prior art ultrasonic sensors.

Previously, people in the art attempted to solve this problem by changing the angle of the ultrasonic sensor with respect to the web material (away from the perpendicular orientation discussed above), as well as designing sensor housing to maintain non-parallelism between transmit and receive sides, so that the sound reflections would be reflected away from the receiver. Although the prior art method reduced the problem of sound reflection somewhat, it is less desirable to have the prior art ultrasonic sensor mounted angularly with respect to the direction of web travel. In addition, this angular mounting limits the effective sensing area and allows less web plane change than that of perpendicular mounting.

Thus, there is a need for an ultrasonic sensor which does not suffer from the aforementioned problems caused by the reflection of the sound waves as described hereinabove. It is to such an improved ultrasonic sensor that the present invention is directed.

SUMMARY OF THE INVENTION

In general, the present invention relates to a sensor system for accurately determining the position of at least one edge of at least one web material. Generally, webbing systems have at least one web material, usually a continuous sheet of either transparent or opaque material, which is moving in a direction of travel generally along a longitudinal axis of the at least one web material. As the at least one web material moves along the longitudinal direction of travel, the at least one web material may deviate in a direction, which is generally transverse or lateral to the direction of travel. The determination of the position of at least one edge of the at least one web material by the sensor system of the present invention can be used to measure and correct for the lateral deviation of the at least one web material so that the at least one web material remains traveling along a predetermined path. In another application, when there is more than one web material present, such as for example in a layering or lamination application, a determination of the position of at least one edge of each of the web materials by the sensor system of the present invention can be used to maintain alignment of the two or more web materials.

Broadly, in one embodiment of the present invention, a sensor system is constructed for through-beam operation. The sensor system comprises at least one transmitter block having a plurality of transmitters arranged in a staggered matrix formation, at least one receiver block having a plurality of receivers arranged in a staggered matrix formation, and a master unit for controlling the plurality of transmitters of the at least one transmitter block and the plurality of receivers of the at least one receiver block.

The plurality of transmitters of the at least one transmitter block are capable of selectively transmitting ultrasonic signals. The plurality of receivers of the at least one receiver block are capable of receiving at least a portion of the ultrasonic signals transmitted by the plurality of transmitters, and in response thereto, generating receiver output signals indicative of the ultrasonic signals received.

The at least one receiver block is disposed opposite the at least one transmitter block and is spaced a distance from the at least one transmitter block so as to define a sensor field of view therebetween. As the at least one web material travels through at least a portion of the sensor field of view, the at least one web material interferes with at least a portion of the ultrasonic signal transmitted by the plurality of transmitters of the at least one transmitter block. Thus, the receiver output signals generated by the plurality of receivers of the receiver block in response to the receiving at least a portion of the ultrasonic signals is indicative of the position of at least a portion of the at least one web material as at least a portion of the at least one web material is moved along a path in between the at least one transmitter block and the at least one receiver block of the sensor system.

The master unit periodically transmits to each of the transmitters of the at least one transmitter block a transmitter drive signal to cause the transmitters to "fire" or transmit periodic ultrasonic signals. In one aspect of the present invention, to reduce undesired reception and noise by each of the receivers, the master unit outputs receiver cutoff signals to selectively toggle each of the receivers in between a first mode, wherein the receiver is permitted to form the receiver output signal responsive to the receiver sensing ultrasonic signals, and a second mode wherein the receiver is restricted from providing the receiver output signal.

In one aspect of the present invention, to reduce interference between the ultrasonic signals transmitted by the plurality of transmitters (of the same or different resonant), the master unit controls the firing sequence and/or frequency of the transmitters so that each transmitter (or group of transmitters) transmits ultrasonic signals at a different time and/or frequency than adjacently disposed transmitters (or groups of transmitters). The master unit also controls the reception sequence of the receivers so that each receiver (or group of receivers) receives ultrasonic signals at a different time than adjacently disposed receivers (or groups of receivers), generally in accordance with the firing sequence of the transmitters.

The master unit receives the receiver output signals generated by the plurality of receivers responsive to the receivers receiving at least a portion of the ultrasonic signals transmitted by the plurality of transmitters. By comparing the receiver output signals to a threshold value (e.g., a "no signal" to "full signal" transition), or by comparing the receiver output signals relative to each other, the master unit can determine the position of at least one edge of the at least one web material and output a sensor output signal indicative of the same. Generally, the comparison provides the web edge vicinity, which is used to establish a proportional band. By measuring the percentage of signal block within the proportional band, at least one edge of the at least one web material is determined. Further, the master unit can determine a width of the at least one web material, and/or transitions between two or more web materials, and generate sensor output signals indicative of the same.

In another embodiment of the present invention, a sensor system is constructed for reflective operation. The sensor system comprises at least one transceiver block having a plurality of transceivers arranged in a staggered matrix formation, at least one reflector, and a master unit for controlling the plurality of transceivers of the at least one transceiver block. The plurality of transceivers of the at least one transceiver block are capable of selectively transmitting ultrasonic signals, and are also capable of receiving at least a portion of the ultrasonic signals and in response thereto, generate receiver output signals indicative of the ultrasonic signals received. The at least one reflector is capable of reflecting at least a portion of the ultrasonic signals transmitted by the plurality of transceivers back to the plurality of transceivers so that at least a portion of the reflected ultrasonic signals can be received by the plurality of transceivers.

The at least one reflector is disposed opposite the at least one transceiver block and is spaced a distance from the at least one transceiver block so as to define a sensor field of view therebetween. As the at least one web material travels through at least a portion of the sensor field of view, the at least one web material interferes with at least a portion of the ultrasonic signals transmitted by the plurality of transceivers of the at least one transceiver block and reflected by the at least one reflector. Thus, the receiver output signals generated by the plurality of transceivers is indicative of the position of at least a portion of the at least one web material as at least a portion of the at least one web material is moved along a path in between the at least one transceiver block and the at least one reflector of the sensor system.

The master unit periodically transmits to each of the transceivers of the transceiver block a transmitter drive signal to cause the transceivers to "fire" or transmit periodic ultrasonic signals. In one aspect of the present invention, to reduce undesired reception and noise by each of the transceivers, the master unit outputs receiver cutoff signals to selectively toggle each of the transceivers in between a first mode wherein the transceiver is permitted to form the receiver output signal responsive to the transceiver sensing ultrasonic signals, and a second mode wherein the transceiver is restricted from providing the receiver output signal.

In one aspect of the present invention, to reduce interference between the ultrasonic signals transmitted by the plurality of transceivers (of the same or different resonant frequency), the master unit controls the firing sequence and/or frequency of the transceivers so that each transceiver (or group of transceivers) transmits ultrasonic signals at a different time and/or frequency than adjacently disposed transceivers (or groups of transceivers). The master unit also controls the reception sequence of the transceivers so that each transceiver (or group of transceivers) receives ultrasonic signals at a different time than adjacently disposed transceivers (or groups of transceivers), generally in accordance with the firing sequence of the transceivers.

The master unit receives the receiver output signals generated by the plurality of transceivers responsive to the transceivers receiving ultrasonic signals. By comparing the receive output signals to a threshold value, or by comparing the receiver output signals relative to each other, the master unit can determine the position of at least one edge of the at least one web material, a width of the at least one web material, and/or transitions between two or more web materials, and generate sensor output signals indicative of the same.

The various advantages of the present invention include, for example, increased sensing accuracy, reduced gaps along a length and/or width of the sensor field of view of the sensor system, increased sensing gap of the sensor field of view, reflective operation, multi-edge sensing, and multi-web sensing. Other advantages and features of the present invention will become apparent to those skilled in the art when the following description is read in conjunction with the attached drawings and the appended claims.

BRIEF DESCRIPTION OF THE DRAWINGS

FIG. 3a is an elevational, diagrammatic view of one embodiment of a transmitter block of the sensor system.

FIG. 3b is a partial, elevational view, in more detail, of one embodiment of an arrangement of a plurality of transmitters of the transmitter block depicted in FIG. 3a.

FIG. 4b is a partial, elevational view, in more detail, of one embodiment of an arrangement of a plurality of receivers of the receiver block depicted in FIG. 4a.

FIG. 10b is a perspective, diagrammatic view of the sensor system depicted in FIG. 10a, wherein two web materials of different acoustic opacity are being sensed.

FIG. 10c is a perspective, diagrammatic view of another embodiment of the sensor system constructed for reflective operation in accordance with the present invention.

FIG. 12b is a partial, elevational view, in more detail, of one embodiment of an arrangement of a plurality of transceivers of the transceiver block depicted in FIG. 12a.

DETAILED DESCRIPTION OF THE INVENTION

Figure 1A:
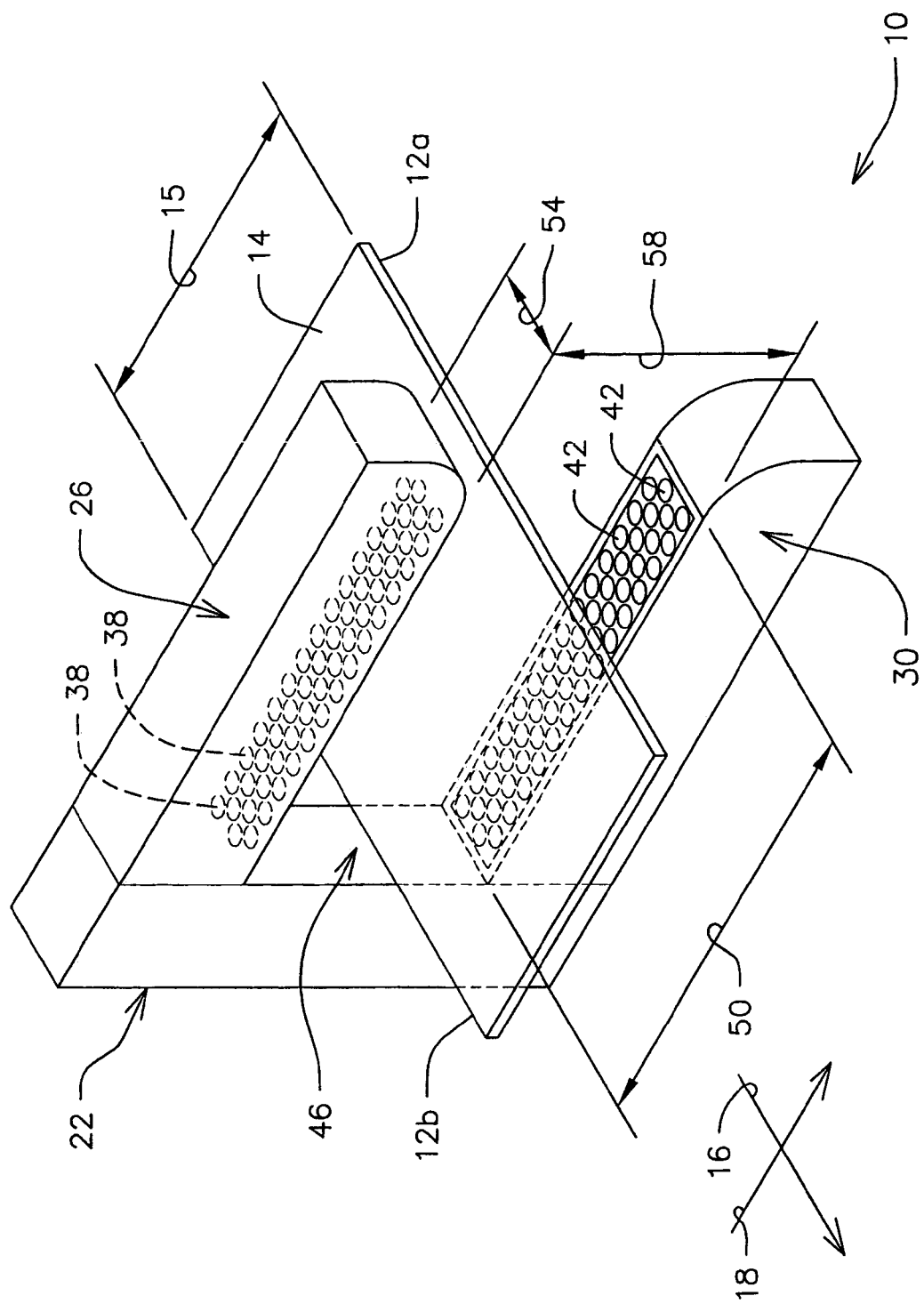
FIG. 1a is a perspective, diagrammatic view of one embodiment of a sensor system constructed for through-beam operation, in accordance with the present invention (wherein one web material is being sensed).

Referring now to the drawings and in particular to FIG. 1a, shown therein is a sensor system 10 which is constructed in accordance with the present invention. The sensor system 10 is adapted and constructed to accurately sense at least one web material 14 so as to determine the position of at least one edge 12 of the at least one web material 14, a width 15 of the at least one web material 14, a transition between two web materials 14, or combinations thereof. In general, the at least one web material 14 is a continuous sheet of transparent or opaque material moving in a web direction of travel 16, which is generally along the longitudinal axis of the at least one web material 14. As the at least one web material 14 moves along the web direction of travel 16, the at least one web material 14 may deviate in a direction 18, which is generally transverse or lateral to the web direction of travel 16.

The sensor system 10 includes a housing 22 which is adapted to receive at least one transmitter block 26 and at least one receiver block 30. The at least one transmitter block 26 of the sensor system 10 includes a plurality of transmitters 38 (shown in phantom, only two being labeled in FIG. 1a for purposes of clarity). Each transmitter 38 is selectively capable of generating ultrasonic signals. The at least one receiver block 30 of the sensor system 10 includes a plurality of receivers 42 (only two being labeled in FIG. 1a for purposes of clarity). Each receiver 42 is selectively capable of receiving ultrasonic signals, and generating a receiver output signal indicative of the ultrasonic signals received.

Figure 2:
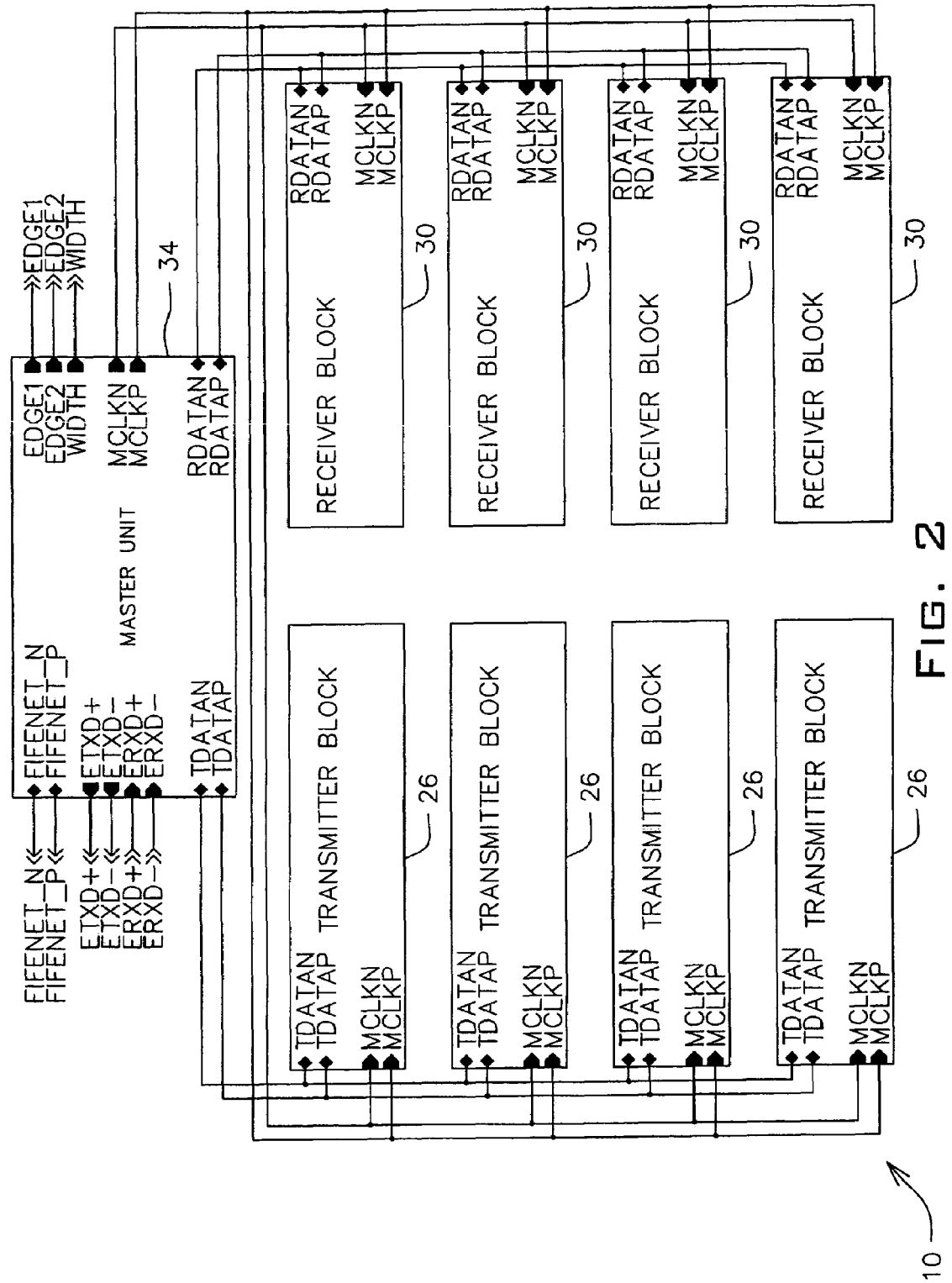
FIG. 2 is a block diagram of one embodiment of a sensor system constructed for through-beam operation in accordance with the present invention.

As best shown in FIG. 2, the sensor system 10 can include more than one transmitter block 26, and more than one receiver block 30. Although the sensor system 10 is shown in FIG. 2 as having four transmitter blocks 26 and four receiver blocks 30, it should be understood that the sensor system 10 can have any number of transmitter blocks 26 and any number of receiver blocks 30. Preferably, the sensor system 10 includes the same number of receiver blocks 30 as there are transmitter blocks 26 in the sensor system 10 so that each receiver block 30 can be paired with a corresponding transmitter block 26. However, it should be understood that the present invention contemplates that more than one transmitter block 26 can be paired or grouped with one receiver block 30, and more than one receiver block 30 can be paired or grouped with one transmitter block 26. Also, as discussed in further detail below, when the sensor system 10 includes paired receiver blocks 30 and transmitter blocks 26, each receiver block 30 will have the same number of receivers 42 as there are transmitters 38 in the paired transmitter block 26 so that each receiver 42 in the receiver block 30 can be paired with a corresponding transmitter 38 in the transmitter block 26.

As shown in FIG. 1a, the housing 22 is preferably mounted perpendicularly with respect to the web direction of travel 16, and the at least one transmitter block 26 and at least one receiver block 30 are on opposite sides of the at least one web material 14 and are disposed such that the ultrasonic signals transmitted by the plurality of transmitters 38 of the at least one transmitter block 26 are substantially projected onto the plurality of receivers 42 of the at least one receiver block 30.

The housing 22 serves to space the at least one transmitter block 26 from the at least one receiver block 30 to form a sensor field of view 46 therebetween. The sensor field of view 46 has a length 50, a width 54, and a sensing gap 58. Preferably, the length 50 of the sensor field of view 46 is greater then the width 15 of the at least one web material 14. However, the length 50 of the sensor field of view 46 can be less than the width 15 of the at least one web material 14, such as for example when only one edge 12 of the at least one web material 14 is being sensed. The width 54 of the sensor field of view generally depends on the size, proportional band, and arrangement of the transmitters 38 of the at least one transmitter block 26 and receivers 42 of the at least one receiver block 30 (as discussed in further detail below). The sensing gap 58 of the sensor field of view 46 extends generally in between the at least one transmitter block 26 and the at least one receiver block 30, and is sufficient to dispose the at least one web material 14 therebetween.

Although the sensor field of view 46 is preferably continuous, it should be understood that the sensor field of view 46 can also be discontinuous. For example, when the sensor system 10 has more than one transmitter block 26 and/or more than one receiver block 30, the transmitter blocks 26 and/or receiver blocks 30 can be staggered or disposed remotely from each other.

In general, as the at least one web material 14 travels through at least a portion of the sensor field of view 46, the at least one web material 14 will interfere with or block the passage of at least a portion of the ultrasonic signals transmitted by the plurality of transmitters 38 because the ultrasonic signals, upon reaching the at least one web material 14, are partially absorbed, reflected, or deflected by the at least one web material 14. Thus, the ultrasonic signals received by each receiver 42 will depend on the relative location of the at least one web material 14 to the receiver 42. As such, and as will be understood by those skilled in the art, the ultrasonic signals received by the receivers 42 of the at least one receiver block 30 are indicative of the position of at least one edge 12 of the at least one web material 14, as well as other information which can be determined therefrom, such as the center position of the at least one web material 14 and transitions between two or more web materials 14. Further, with real-time sensing, deviations of the at least one web material 14 in the direction 18 can be detected as the at least one web material 14 moves through at least a portion of the sensor field of view 46.

Each of the transmitters 38 of the at least one transmitter block 26 can be any transducer capable of generating ultrasonic signals in response to the receipt of electrical signals. For example, each of the transmitters 38 can be an ultrasonic transmitter or an ultrasonic transceiver operating in transmitter mode. In one embodiment, when each of the transmitters 38 are of the same resonant frequency, each transmitter 38 can be a MA200D1 High-Frequency Ultrasonic Sensor, having an operating frequency range from about 220 kHz±about 20 kHz, available from Murata Manufacturing Co., Ltd. of Japan. However, it should be understood that each of the transmitters 38 can operate in another frequency range. For example, a frequency range can be selected so as to eliminate interference from expected environmental sound waves (e.g. from machinery or other nearby sensor systems). Also, the plurality of transmitters 38 do not have to operate at the same frequency. For example, each transmitter 38 can have a different operating frequency than an adjacently or nearly disposed transmitter 38 in the same transmitter block 26 or in another adjacently disposed transmitter block 26 so as to help reduce interference between ultrasonic signals generated by two or more transmitters 38.

Preferably, each transmitter 38 of the at least one transmitter block 26 is a discrete unit that can be independently disposed in and supported by the housing 22, and has its own sound conducting material, which can be made of silicon or teflon, for example. As such, it should be understood that each transmitter 38 of the at least one transmitter block 26 can be isolated from the other transmitters 38 and disposed on a different plane. Further, the at least one transmitter block 26 may also include sound insulation material 59 (as shown for example in FIG. 3a), such as for example rubber or foam material, disposed substantially around a portion of each of the transmitters 38 so as to insulate the transmitters 38 from undesired signals and vibrations (e.g. from the housing 22) while allowing the transmitters 38 to transmit ultrasonic signals to the receivers 42 of the at least one receiver block 30. Such undesired signals can include, for example, external sound waves (such as from other equipment near the sensor system 10), deflected ultrasonic signals (such as from the housing 22), and other noise or vibrations (such as from the housing 22). In one preferred embodiment, the sound insulation material 59 is disposed around a portion of each of the transmitters 38 such that each transmitter 38 remains independent and thus further insulated from adjacently disposed transmitters 38 in the at least one transmitter block 26.

Figure 1B:
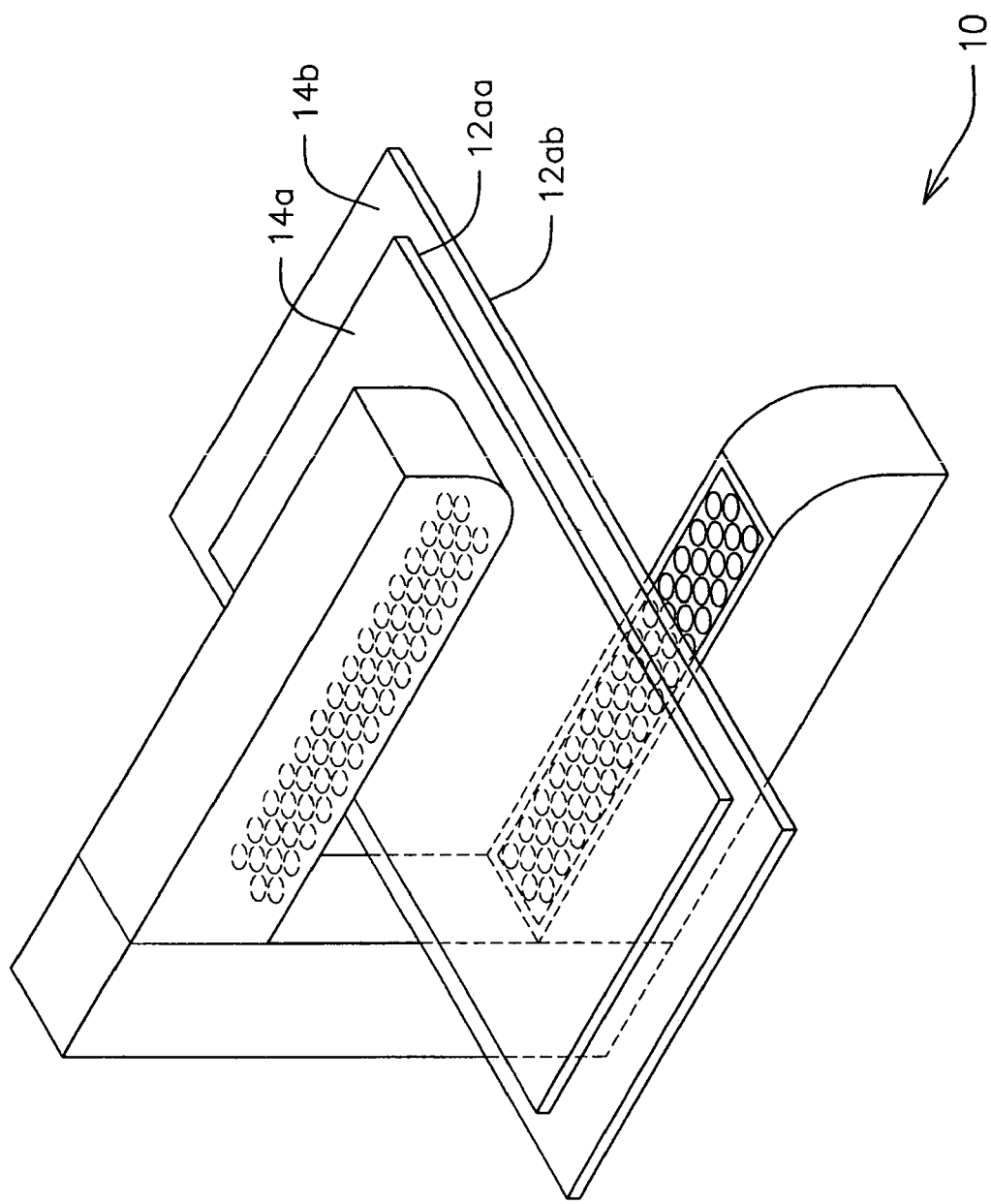
FIG. 1b is a perspective, diagrammatic view of the sensor system depicted in FIG. 1a, wherein two web materials of different acoustic opacity are being sensed.
Figure 1C:
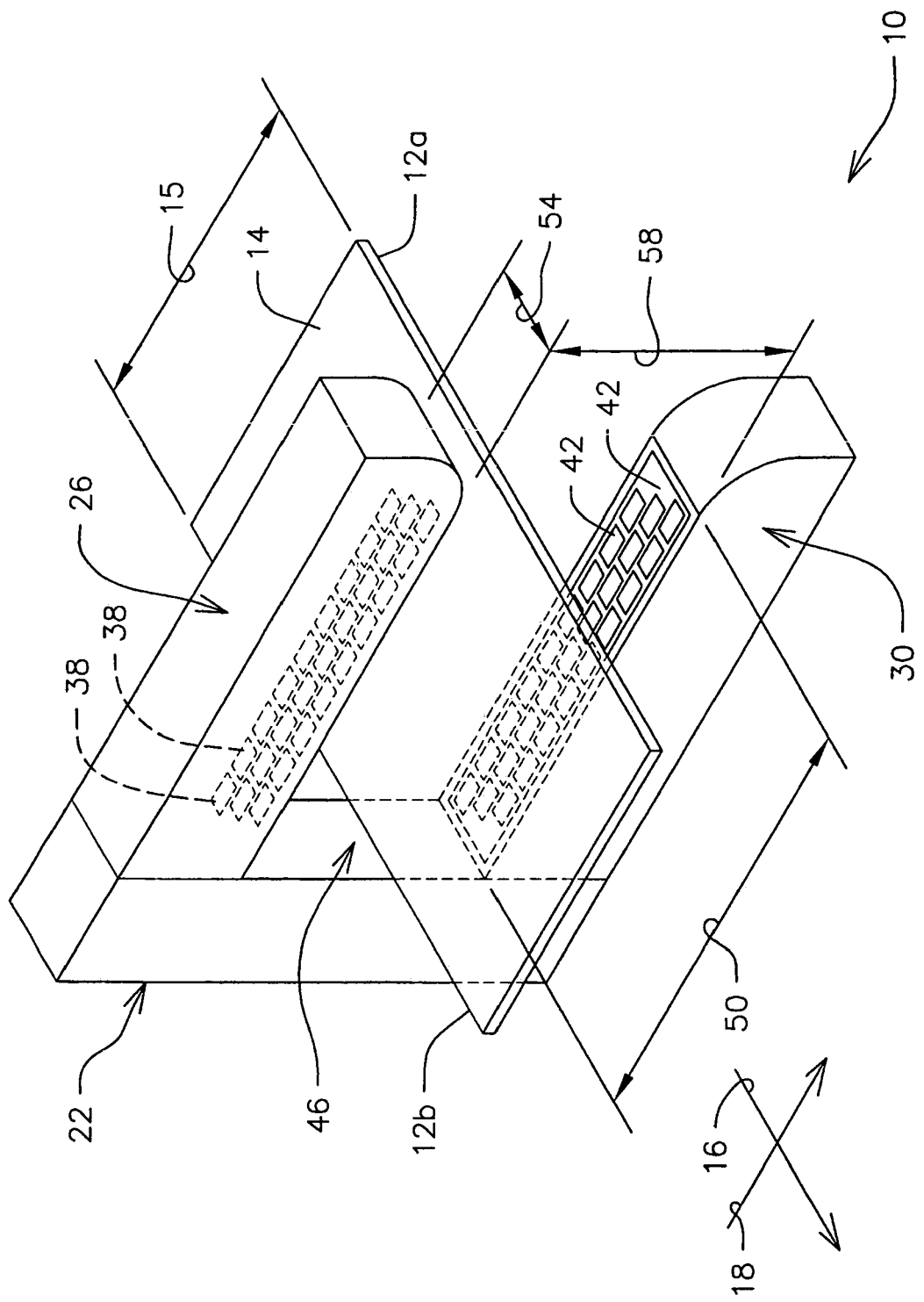
FIG. 1c is a perspective, diagrammatic view of another embodiment of the sensor system constructed for through-beam operation, in accordance with the present invention.

In one preferred embodiment, the transmitters 38 have a symmetric circular shape, such as shown for example in FIG. 1a. However, it should be understood that the transmitters 38 can have any shape, and can be either symmetric or asymmetric, generally depending on the desired beam profile of the produced ultrasonic signals. For example, as shown in FIG. 1c, the transmitters 38 may have an asymmetric rectangular shape.

In one embodiment, the plurality of transmitters 38 are arranged in the at least one transmitter block 26 in a staggered matrix formation, as shown best in FIG. 3a. In the staggered matrix formation, the transmitters 38 are disposed in staggered rows, whereby each transmitter 38 in the rows effectively increases a length 60 of the at least one transmitter block 26 and each staggered row effectively increases a width 62 of the at least one transmitter block 26. Although the at least one transmitter block 26 is shown in FIG. 3a as having seven staggered rows of transmitters 38, with each row having eight transmitters 38, it should be understood that the at least one transmitter block 26 may have any number of transmitters 38 in each row of the staggered matrix formation, and the at least one transmitter block 26 can have any number of rows of transmitters 38. Further, each row may have the same or a different number of transmitters 38 as an adjacently disposed row of transmitters 38.

Arranging the transmitters 38 in the staggered matrix formation effectively reduces "gaps" or spaces where there is an absence of ultrasonic signals transmitted by the plurality of transmitters 38 of the at least one transmitter block 26 across at least one of the length 50 or the width 54 of the sensor field of view 46, through which at least a portion of the at least one web material 14 passes and is being sensed. In general, when a sensor has multiple transmitters and receivers, gaps in the sensor's field of view can occur from spacing between transmitters or receivers as well as from practical limitations of real-world transmitters and receivers, such as geometric dimensions and shapes available, actual effective transmission or reception areas, and proportional band or near-linear operation parameters. Gaps reduce the precision and accuracy in the sensing of a web material with respect to all dimension within a sensor's field of view. These effects on sensing performance also generally increase the closer a web material is to the transmitters and receivers because an edge of the web material is more likely to be located within such a gap where there is an absence of the transmission or reception of the ultrasonic signals.

However, in the staggered matrix arrangement of the present invention, the plurality of transmitters 38 of the at least one transmitter block 26 provide a more continuous sensor field of view 46 of the sensor system 10 during real-time sensing of the at least one web material 14. This more continuous sensor field of view 46 provides more flexibility in the positioning of the at least one web material 14 within the sensor field of view 46, including along the sensing gap 58. Further, the staggered matrix arrangement provides more flexibility in the alignment of the web direction of travel 16 of the at least one web material 14 to the sensor system 10, i.e. the sensor system 10 can be used in a non-perpendicular alignment application.

Preferably, the transmitters 38 of the at least one transmitter block 26 are positioned near to adjacently disposed transmitters 38 so to decrease the distance between adjacently disposed transmitters while still allowing for mounting and support by the housing 22 for the transmitters 38, and if desired, the insulating material 59. In one preferred embodiment, each transmitter 38 is arranged in the staggered matrix formation such that at least one edge of a proportional band area of the transmitter 38 is substantially aligned with at least one edge of a proportional band area of an adjacently disposed transmitter 38 and/or at least one edge of a proportional band area of another transmitter 38 along the length 60 of the transmitter block 26, such that gaps along the overall sensing length 60 of the transmitter block 26 are essentially reduced. Preferably, the edges of the proportional band areas are aligned such that the proportional band areas overlap. Overlapping helps to remove gaps and to compensate for such other factors as manufacturing tolerance allowances of other elements of the sensor system 10, such as for example the housing 22 and transmitters 38. Therefore, in such an embodiment, the positioning of the transmitters 38 will generally depend on the physical shape, dimensions, and proportional band area of each of the transmitters 38. In one embodiment, the proportional band area of each transmitter 38 is defined by the 10%-90% near-linear performance of the transmitter 38. However, other limits and/or considerations may be used to define the proportional band area of each of the transmitters 38.

For example, as shown in FIG. 3b, each of the transmitters 38 has a 0.75 inch diameter and an effective proportional band area of 0.25 inches as defined by a start point 63 and an end point 64. Because the disposition of the transmitters 38 is repetitive, for purposes of clarity, the disposition of only four transmitters 38a, 38b, 38c, and 38d will be discussed in further detail. An end point 64a of the proportional band area of transmitter 38a is aligned with a start point 63b of the proportional band area of transmitter 38b so as to overlap by 0.025 inches along the length 60 of the transmitter block 26. An end point 64b of the proportional band area of transmitter 38b is aligned with a start point 63c of the proportional band area of transmitter 38c so as to overlap by 0.025 inches along the length 60 of the transmitter block 26. An end point 64c of the proportional band area of transmitter 38*c* is aligned with a start point 63*d* of a proportional band of transmitter 38*d* so as to overlap by 0.025 inches along the length 60 of the transmitter block 26.

Therefore, it can be seen that the alignment and overlap of the plurality of transmitters 38 along the length 60 of the at least one transmitter block 26 essentially reduces gaps along the length of the at least one transmitter block 26. Although the transmitters 38 are discussed herein as being arranged so as to reduce gaps along the length 60 of the at least one transmitter block 26, it should also be understood that the same method of alignment of the transmitters 38 can be applied along the width 62 of the at least one transmitter block 26. Also, because of real-world client requests to reduce the number of transmitters 38 (e.g. to reduce costs), the present invention contemplates that not all gaps along the length 60 and/or width 62 of the at least one transmitter block 26 have to be reduced when disposing the transmitters 38 in the staggered matrix formation. Further, the present invention contemplates that at least some of the start points 63 and end points 64 of the proportional band areas may be aligned such that the proportional band areas are spaced a minimal distance apart rather than being overlapped.

Therefore, it can be seen that in general the number of transmitters 38 in each row and the number of rows of transmitters 38 in the staggered matrix formation of the at least one transmitter block 26 can depend on various considerations, such as the intended application of the sensor system 10, the dimensions of the at least one web material 14 or portions thereof being sensed, the dimensions of each of the transmitters 38, allowance for gaps in the transmitter block 26, the desired dimensions of the sensor field of view 46, the number of transmitter blocks 26 and receiver blocks 26 included in the sensor system 10, costs, etc.

Each of the receivers 42 of the at least one receiver block 30 can be any transducer capable of generating electrical signals in response to the receipt of ultrasonic signals. For example, when each of the receivers 42 are of the same resonant frequency, each receiver 42 can be an ultrasonic receiver or an ultrasonic transceiver operating in receiver mode. In one embodiment, each of the receivers 42 can be a MA200D1 High-Frequency Ultrasonic Sensor, having an operating frequency range from about 220 kHz±about 20 kHz, available from Murata Manufacturing Co., Ltd. of Japan. However, similar to the transmitters 38, it should be understood that each of the receivers 42 can operate in another frequency range (generally at the frequency of a corresponding transmitter 38), and the plurality of receivers do not have to operate at the same frequency.

Similar to each of the transmitters 38, each receiver 42 of the at least one receiver block 30 is preferably a discrete unit that can be independently disposed in and supported by the housing 22, and has its own sound conducting material. As such, it should be understood that each receiver 42 of the at least one receiver block 30 can be isolated from the other receivers 42 and disposed on a different plane. Further, the at least one receiver block 30 may also include sound insulation material 65 (such as shown for example in FIG. 4*a*), such as for example rubber or foam material, disposed substantially around a portion of each of the receivers 42 so as to insulate each receiver 42 from adjacent receivers 42, as well as from undesired signals and vibrations (e.g. from the housing 22), while allowing the receivers 42 to receive ultrasonic signals transmitted by the transmitters 38 of the transmitter block 26. Such undesired signals can include, for example, external sound waves (such as from other equipment near the sensor system 10), deflected ultrasonic signals (such as from the housing 22), and other noise or vibrations (such as from the housing 22). In one preferred embodiment, the sound insulation material 65 is disposed around a portion of each of the receivers 42 such that each receiver 42 remains independent and thus further insulated from adjacently disposed receivers 42 in the at least one receiver block 30.

In one preferred embodiment, the receivers 42 have a symmetric circular shape, such as shown for example in FIG. 1*a*. However, it should be understood that the receivers 42 can have any shape, and can be either symmetric or asymmetric, depending on the beam profile of the ultrasonic signals being received. For example, as shown in FIG. 1*c*, the receivers 42 may have an asymmetric rectangular shape.

Figure 4A:
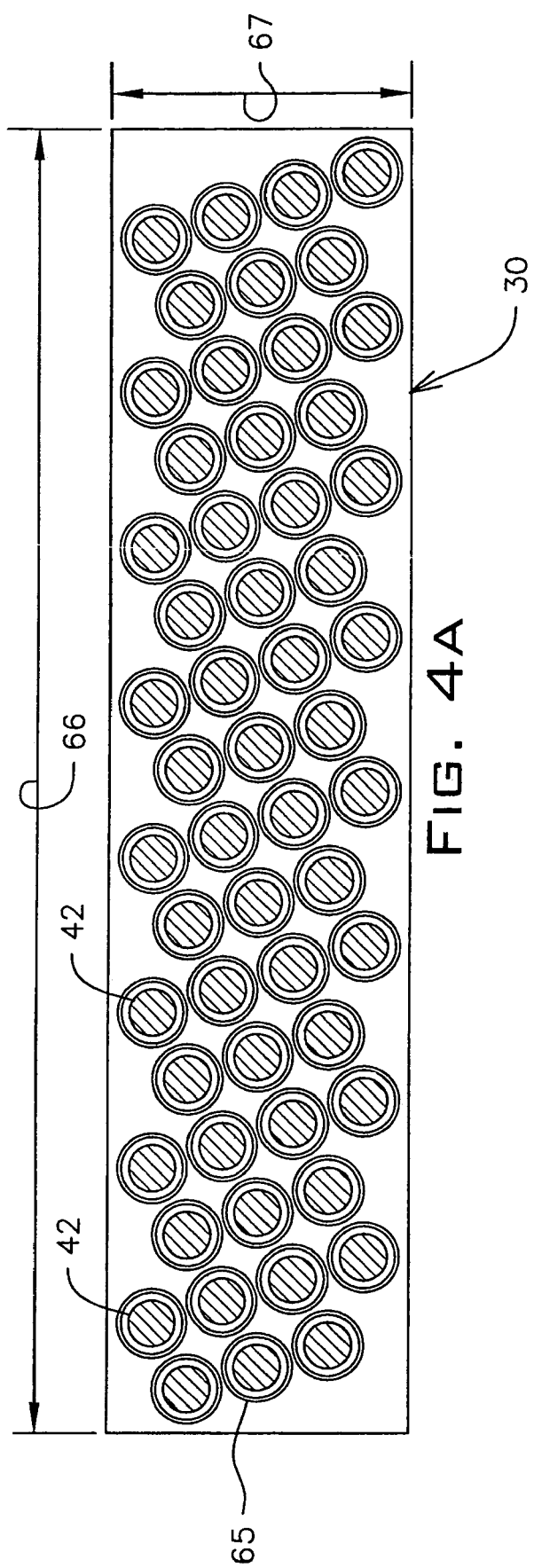
FIG. 4a is an elevational, diagrammatic view of one embodiment of a receiver block of the sensor system.

In one embodiment, as shown best in FIG. 4*a*, the plurality of receivers 42 are arranged in the at least one receiver block 30 in a staggered matrix formation in a manner similar to the plurality of transmitters 38 of the at least one transmitter block 26. In the staggered matrix formation, the receivers 42 are disposed in staggered rows, whereby each receiver 42 in the rows effectively increases a length 66 of the at least one receiver block 30, and each staggered row effectively increases a width 67 of the at least one receiver block 30. In a similar manner as the transmitters 38, placing the receivers 42 in a staggered arrangement effectively reduces gaps where there is an absence of ultrasonic signals received by the plurality of receivers 42 of the at least one receiver block 30 across at least one of the length 50 or the width 54 of the sensor field of view 46, through which at least a portion of the at least one web material 14 passes and is being sensed.

Although the at least one receiver block 30 is shown in FIG. 4*a* as having seven staggered rows of receivers 42, with each row having eight receivers 42, it should be understood that the receiver block 30 may have any number of receivers 42 in each row of the staggered matrix formation, and the receiver block 30 may have any number of rows of receivers 42. Further, each row may have the same or a different number of receivers 42 as an adjacently disposed row of receivers 42. The number of receivers 42 in each row and the number of rows of receivers 42 included in the at least one receiver block 30 generally depends on various considerations, such as the number of transmitters 38 in the transmitter block 26, the number of transmitter blocks 26 and receiver blocks 30 included in the sensor system 10, the intended application of the sensor system 10, the dimensions of the at least one web material 14 or portion thereof being sensed, the dimensions of each of the receivers 42, allowance for gaps in the receiver block 30, the desired sensor field of view 46 dimensions, costs, etc. Preferably however, when the sensor system 10 includes at least one transmitter block 26 paired with one receiver block 30, each receiver block 30 includes the same number of receivers 42 as there are transmitters 38 in the corresponding transmitter block 26 so that each of the receivers 42 of the receiver block 30 can be paired with a corresponding transmitter 38 of the corresponding transmitter block 26. In such an embodiment, each receiver 42 of the receiver block 30 is positioned and constructed to receive at least a portion of the ultrasonic signal 36 transmitted by a paired transmitter 38 disposed generally opposite the receiver 42.

Figure 4B:
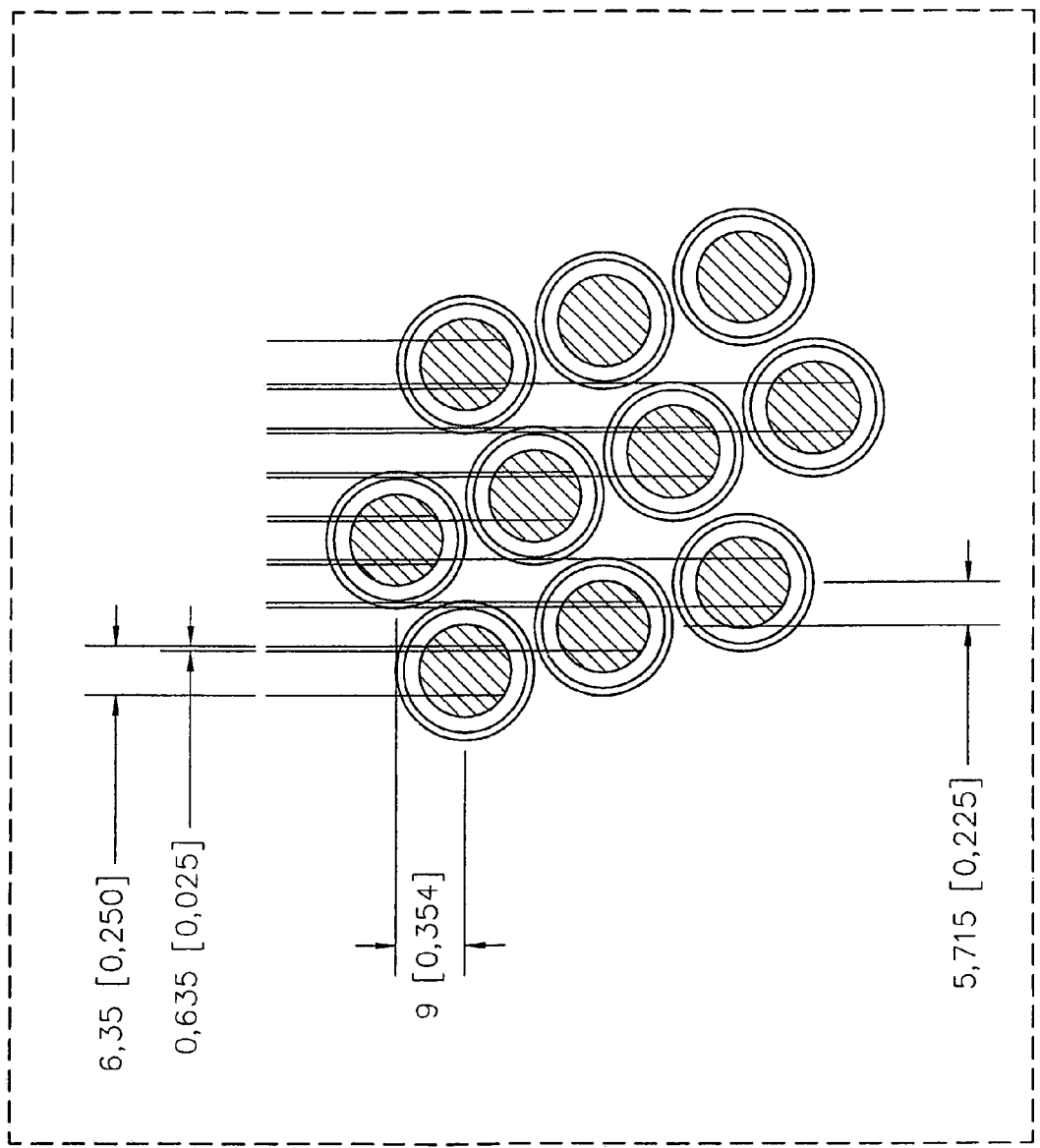
Figure 5A:
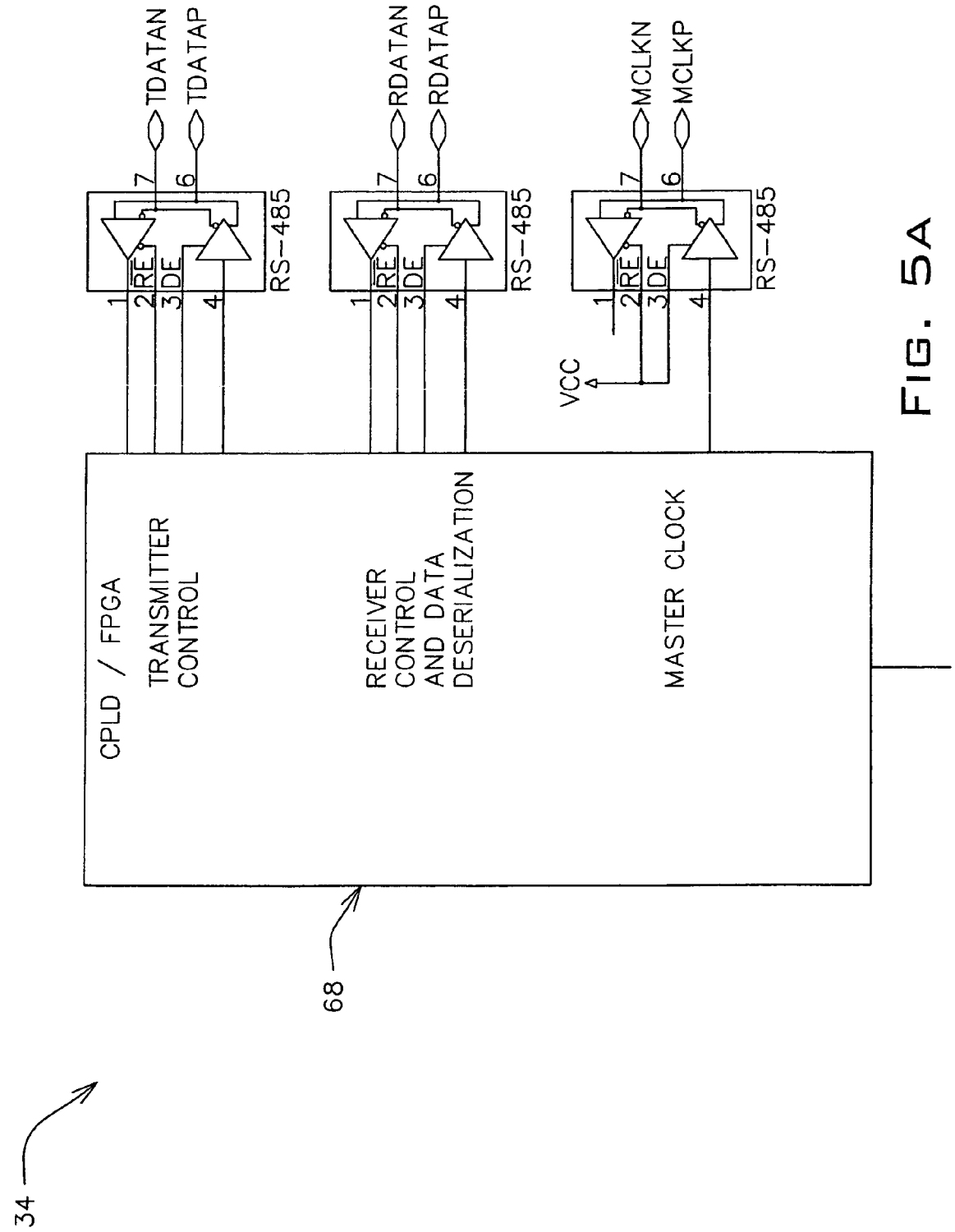

Preferably, the positioning of each of receivers 42 in the at least one receiver block 30 mirrors that of the corresponding transmitter 38 in the corresponding transmitter block 26. As such, it can be seen that the number of rows and the number of receivers 42 in each row of the receiver block 30 will correspond to the number of rows and number of transmitters 38 in each row of the corresponding transmitter block 26 and the disposition of the receivers 42 will be substantially the same as discussed above for the transmitters 38. For example, to mirror the transmitters 38 shown in FIG. 3b, the receivers 42 shown in FIG. 4b, which have a 0.75 inch diameter and a proportional band area of 0.25 inches are overlapped by 0.025 inches along the length 66 of the at least one receiver block.

Although the sensor system 10 is generally discussed herein as having one transmitter 38 paired to one receiver 42, it should be understood that the present invention contemplates that more than one transmitter 38 can be paired or grouped with one receiver 42, and more than one receiver 42 can be paired or grouped with one transmitter 38.

As shown in FIG. 2, the sensor system 10 also includes a master unit 34, which communicates with the at least one transmitter block 26 and the at least one receiver block 30 to control the plurality of transmitters 38 and the plurality of receivers 42. The master unit 34 periodically transmits to each of the transmitters 38 of the at least one transmitter block 26 a transmitter drive signal to selectively cause the transmitters 38 to "fire" or transmit periodic ultrasonic signals. In one embodiment, to reduce undesired reception and noise by each of the receivers 42, the master unit 34 also selectively outputs receiver cutoff signals to each of the receivers 42 so as to selectively toggle the receiver 42 in between a first mode wherein the receiver 42 is "on" and permitted to form the receiver output signal responsive to the receiver 42 sensing ultrasonic signals, and a second mode wherein the receiver 42 is "off" and restricted from providing the receiver output signal. For each receiver 42, toggling between the "on" and "off" modes is the same, therefore for purposes of clarity, the toggling of only one receiver 42 is discussed in further detail below.

In one embodiment, the receiver cutoff signal is continuously maintained in the second mode so as to turn the receiver 42 "off", and selectively toggled to the first mode to turn the receiver 42 "on" for a predetermined time coincident with the transmitting of the transmitter drive signal or a corresponding transmitter 38 so that the receiver 42 can generate the receiver output signal. After the predetermined time has passed, the master unit 34 automatically toggles the receiver cutoff signal from the first mode to the second mode to turn the receiver 42 "off" to restrict the receiver 42 from generating any noise.

To minimize interference between transmitters 38, the master unit 34 can further control the firing sequence and/or frequency of the transmitters 38 so that each transmitter 38 (or group of transmitters 38) transmits ultrasonic signals at a different time and/or frequency than adjacently disposed transmitters 38 (or groups of transmitters 38). For example, the master unit 34 can synchronize the transmitter drive signals sent to two or more transmitters 38 of the at least one transmitter block 26. The master unit 34 can also control the reception sequence of the receivers 42 so that each receiver 42 (or group of receivers 42) receives ultrasonic signals at a different time than adjacently disposed receivers 42 (or groups of receivers 42), generally in accordance with the firing sequence of a corresponding transmitter 38. For example, the master unit 34 can synchronize the receiver cutoff signals sent to two or more receivers 42 of the at least one receiver block 30. Further, the master unit 34 can synchronize the transmitter drive signal sent to at least one transmitter 38 and receiver cutoff signal sent to at least one receiver 42, such as a paired transmitter 38 and receiver 42 (as discussed above). Also, when the sensor system 10 includes more than one transmitter block 26 and/or receiver block 30, the master unit 34 can synchronize the transmitter drive signals outputted to the transmitter blocks 26 and/or the receiver cutoff signals outputted to the receiver blocks 30 so as to reduce interference between the transmitters 38 of two or more transmitter blocks 26 and/or receivers 42 of two or more receiver blocks 30.

The term "synchronize", and derivations thereof, is used herein to refer to a timing relationship. "Synchronize" can mean to cause to happen, exist, or arise at precisely the same time or within a certain time period of each other.

In addition to controlling the plurality of transmitters 38 of the at least one transmitter block 26 and receivers 42 of the at least one receiver block 30, the master unit 34 may also be adapted to send and receive diagnostic data from each of the transmitters 38 and/or each of the receivers 42.

The master unit 34 also receives the receiver output signals generated by the plurality of receivers 42. In one embodiment, the master unit 34 utilizes the receiver output signals outputted by the receivers 42 to generate sensor output signals indicative of the position of at least one edge 12 of the at least one web material 14 by setting a threshold value to which the receiver output signals are compared. The threshold value is generally set such that when each receiver output signal from each receiver 42 is compared to the threshold value, the comparison indicates whether at least a portion of the ultrasonic signals generated by a corresponding transmitter 38 was interfered with and thus not received by the corresponding receiver 42. As such, the comparison of the receiver output signals of the receivers 42 and the threshold value can be utilized by the master unit 34 to determine the position of at least one edge 12 of the at least one web material 14 within the sensor field of view 46. Generally, the receiver output signals are compared to the threshold value (e.g., a "no signal" to "full signal" transition) so as to locate the web edge vicinity, which is used to establish a proportional band. Then, by measuring the percentage of signal block within the proportional band, the position of at least one edge 12 of the at least one web material 14 is determined. Also, other information can be determined therefrom, such as the center position of the at least one web material 14 and/or transitions between two or more web materials 14.

In another embodiment, the master unit 34 utilizes the receiver output signals outputted by the receivers 42 to generate sensor output signals indicative of the position of at least one edge 12 of the at least one web material 14 by comparing the receiver output signals relative to each other. By comparing the receiver output signals, the master unit 34 can determine the relative amount of ultrasonic signals that were received by each receiver 42. As such, the relative comparison of the output receiver signals can be utilized by the master unit 34 to determine the position of at least one edge 12 of the at least one web material 14 within the sensor field of view 46 by evaluating transitions between receiver output signal values. Also, other information can be determined therefrom, such as the center position of the at least one web material 14 and transitions between two or more web materials 14.

By comparing the receiver output signals to a threshold value, or by comparing the receiver output signals relative to each other, the master unit 34 can determine the position of at least one edge 12 of the at least one web material 14, a width 15 of the at least one web material 14, a transition between two or more web materials 14, or combinations thereof, and generate at least one sensor output signal indicative of the same. For example, the master unit 34 may generate a sensor output signal indicative of the position of a first edge 12a of the at least one web material 14. In another example, the master unit 34 may output at least two sensor output signals, wherein at least one sensor output signal is indicative of the first edge 12a of the at least one web material 14, and at least one other sensor output signal is indicative of another edge 12b of the at least one web material 14. Further, the master unit 34 can output a sensor output signal indicative of the width 15 of the at least one web material 14 by determining the distance between the two edges 12a and 12b of the at least one web material 14. In another example, such as shown in FIG. 1b, when two web materials 14a and 14b of different acoustic opacity (such as for example a spunbound material and an opaque material) are being sensed by the sensor system 10, the master unit 34 can use the receiver output signals to determine the position of an edge 12aa of the first web material 14a. The master unit 34 can also compare the receiver output signals to detect a relative transition in the receive output signals so as to determine the position of an edge 12ab of the second web material 14b, and thereby determine a transition between the two web materials 14a and 14b.

It should also be understood that the information received from comparing the receiver output signals to a threshold value, or by comparing the receiver output signals relative to each other, can further be used in other applications of the sensor system 10, such as for example sensing holes or perforations in the at least one web material 14.

The at least one sensor output signal can be outputted by the master unit 34 to other devices (not shown), such as a for example a conventional web guiding signal processor or computer, which may be in communication with the sensor system 10. It will be appreciated that computers or other serial or parallel connected peripheral devices receiving the at least one sensor output signal may use the at least one sensor output signal for the purpose of controlling the lateral position of the at least one web material 14. For example, adjustments to the at least one web material 14 in the direction 18 with a motor controlled pivotal platform (not shown) can be made in response to the sensor output signal which is indicative of the position of at least one edge 12 of the at least one web material 14. Such adjustments can be made for example to maintain the at least one web material 14 traveling along a predetermined and desired travel path. The sensor output signals received by such devices may also be used for other purposes such as for example web width measurement, tension control, or alignment of the at least one web material 14.

The sensor system 10 can also be connected to a serial bus for a wider range of applications to support features, such as for example web width monitoring and output for other process control besides guiding (such as tension control), web centerline calculations, machine center calculations and calibrations, web centerline shift with respect to calibrated machine center anywhere within the sensor field of view 46, display amount of relative web centerline shift with respect to a machine center, near instantaneous web seeking, programmable web centerline shift speed, and/or user interface for basic web guiding and positioning.

Figure 5:
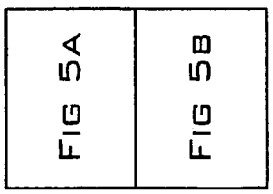
FIG. 5 is a block diagram of one embodiment of a master unit of the sensor system.

Referring now to FIG. 5, shown therein is one embodiment of the master unit 34 of the sensor system 10. The master unit 34 includes a controller 67 and a control circuit 68 to output control data to the plurality of transmitters 38 and receivers 42, and to receive data from the plurality of transmitters 38 and receivers 42, such as diagnostic data or sensing data. More specifically, the controller 67 cooperates with the control circuit 68 so that the master unit 34 selectively outputs transmitter drive signals to the plurality of transmitters 38 of the at least one transmitter block 26, selectively outputs receiver cutoff signals to the plurality of receivers 42 of the at least one receiver block 30, and selectively receives receiver output signals outputted by the plurality of receivers 42 of the receiver block 30.

In one embodiment, the controller 67 of the master unit 34 is a microcontroller, such as for example a microcontroller with an ARM9 microprocessor core, available from Atmel Corporation of San Jose, Calif. The control circuit 68 of the master unit 34 is a complex programmable logic device (CPLD) or field-programmable gate array (FPGA), which includes data registers for adder-corrected clock synchronization. Preferably, the control circuit 68 of the master unit 34 further includes a master clock for synchronization purposes (as discussed further below).

The master unit 34 may further include a plurality of network interfaces 69, such as for example a bidirectional bus or ethernet connection, so as to be in communication with a network area. For example, when the sensor system 10 includes more than transmitter block 26 and/or receiver block 30, the master unit 34 can synchronize the transmitter drive signals outputted to each transmit block 26 and/or the receiver cutoff signals outputted to each receiver block 30 via one of the network interfaces 69 so as to minimize interference between the transmitter blocks 26 and/or receiver blocks 30. Also, the network interfaces 69 can be used to communicate with other sensor systems 10 and/or other devices.

The master unit 34 can also include a temperature compensation circuit 70 for sensing and compensating for environmental temperature. Because the transmitters 38, the receivers 42, and various other components of the sensor system 10 may be sensitive to changes in temperature, the master unit 34 can be adapted to correct the receiver output signals for changes in the environmental temperature surrounding the sensor system 10. This temperature compensation provides for a more accurate sensing of the at least one web material 14. In one embodiment, the temperature compensation circuit 70 includes at least one temperature sensor 71 and an analog-to-digital converter 72. The temperature sensor 71 generates a temperature signal indicative of the absolute temperature surrounding the sensor system 10, which is outputted to the master unit 34 via the analog-to-digital converter 72. The master unit 34 receives the receiver output signals from the receiver block 30 and the temperature signal from the temperature sensor 71. In response thereto, the master unit 34 utilizes at least one of a plurality of stored temperature compensation values to generate sensor output signals which more accurately indicate the position of the of the at least one web material 14. Such a temperature compensation circuit, and the operation thereof, is discussed in further detail in U.S. Pat. No. 6,289,729, entitled "Ultrasonic Sensor for Web-Guiding Apparatus", the contents of which are expressly incorporated herein by reference.

Generally, the plurality of stored temperature compensation values will be the same for receivers 42 that are of similar size, manufacture, and frequency range. Therefore, if different types of receivers 42 are used or if the receivers 42 operate at different frequency ranges, different temperature compensation values may be stored to generate sensor output values accordingly.

While the temperature compensation circuit 70 has been described as being included in the master unit 34, it should be understood that the temperature compensation circuit 70 (or the at least one temperature sensor 71) may be included in the transmitter block 26 or receiver block 30 so as sense the temperature in an area closer to the transmitters 38 or receivers 42, respectively, especially if significant temperature gradients may be expected over the sensor field of view 46.

The master unit 34 may further include an analog output circuit 73 for outputting the sensor output signals to other devices, such as a for example a conventional web guiding signal processor or computer (not shown), which may be in communication with the sensor system 10 (as discussed above). In one embodiment, the analog output circuit 73 includes a first E/I converter 74, a second E/I converter 75, a third E/I converter 76, and a digital-to-analog converter 77. The master unit 34 outputs a signal which is indicative of the location of the first edge 12a of the web material 14 to the first E/I converter 74 via the digital-to-analog converter 77. The master unit 34 outputs a signal which is indicative of the location of the second edge 12b of the web material 14 to the second E/I converter 75 via the digital-to-analog converter 77. Similarly, the master unit 34 outputs a signal which is indicative of the width 15 of the at least one web material 14 to the third E/I converter 76 via the digital-to-analog converter 77.

The first E/I converter 74 outputs an enhanced sensor output signal indicative of the first edge 12a so that such sensor output signal can be received by the conventional web guiding signal processor. The second E/I converter 75 outputs an enhanced sensor output signal indicative of the second edge 12b so that such sensor output signal can be received by the conventional web guiding signal processor. The third E/I converter 76 outputs an enhanced signal indicative of the web width 15 so that such signal can be received by the conventional web guiding signal processor. That is, the E/I converters 74, 75, and 76 convert the analog signals received from the digital-to-analog converter 77 and output current signals. These signals can be voltage-to-current converted signals having a range of between 0-20 milliamperes.

While the signals output by the analog output circuit 73 are described as being outputted as current signals, it should be understood that the output signals from the master unit 34 may be converted into any desirable format required by a particular web guide control system.

Figure 6:
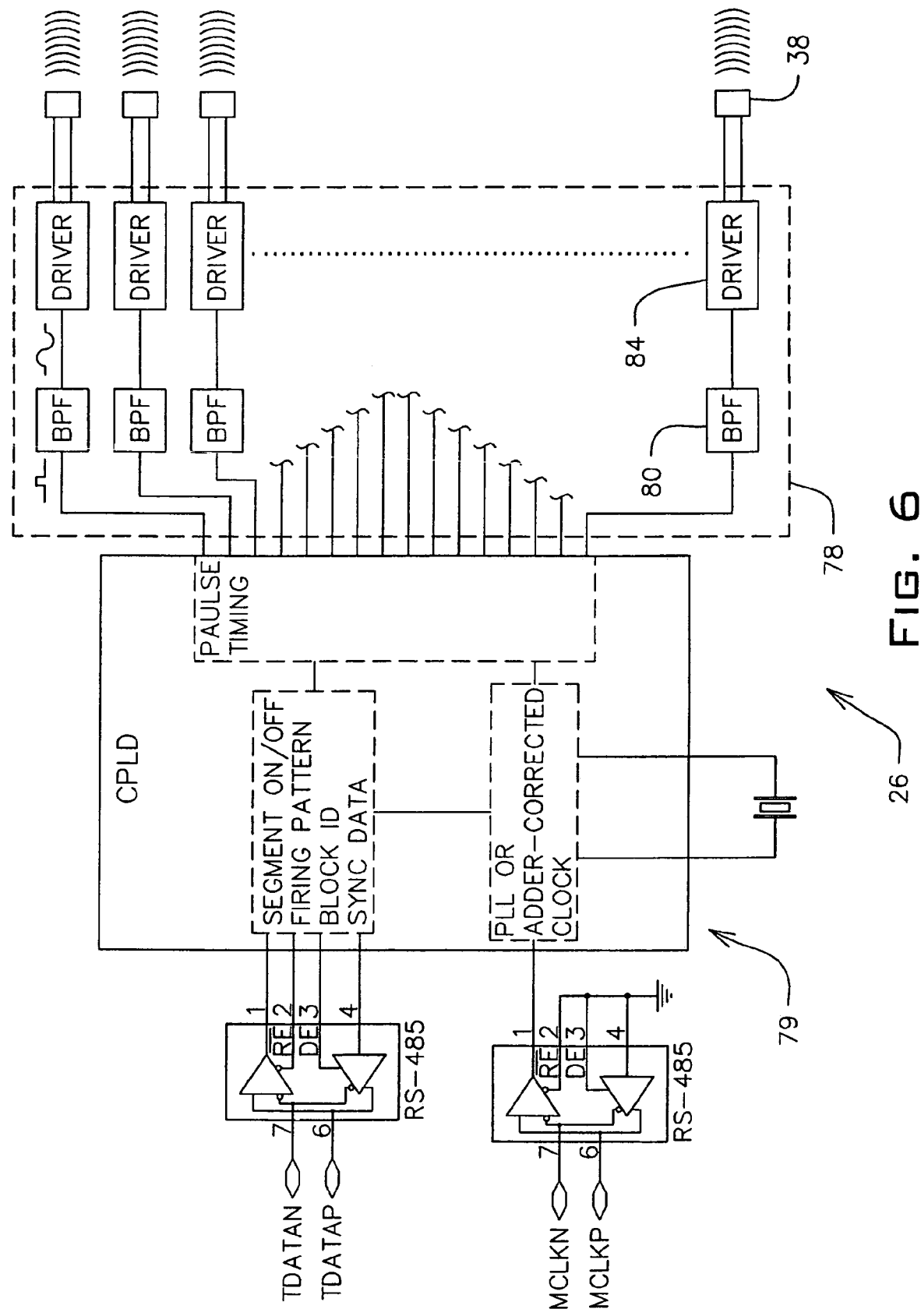
FIG. 6 is a block diagram of one embodiment of a transmitter block of the sensor system.

Referring now to FIG. 6, shown therein in block diagram form is one embodiment of one transmitter block 26 constructed in accordance with the present invention. The transmitter block 26 includes the plurality of transmitters 38 (only one being labeled for purposes of clarity), wherein each transmitter 38 is selectively capable of generating ultrasonic signals in response to the transmitter drive signal outputted by the master unit 34 to the transmitter 38. Although the transmitter block 26 is shown in FIG. 6 as including sixteen transmitters 38, it should be understood that the transmitter block 26 can have any number of transmitters 38.

In one preferred embodiment, the transmitter block 26 further includes a transmit circuit 78 and a data transmission circuit 79 to exchange data between the master unit 34 and the plurality of transmitters 38. In general, the transmit circuit 78 and data transmission circuit 79 cooperate with the master unit 34 to set and synchronize timing patterns for the transmitters 38, to fire the transmitters 38, and to identify or diagnose the transmitters 38 of the at least one transmitter block 26. More particularly, the data transmission circuit 79, which can be for example a complex programmable logic device (CPLD), cooperates with the master unit 34 to control which transmitter 38 (or group of transmitters 38) receives the transmitter drive signal, and the transmit circuit 78 conditions the transmitter drive signal before the transmitter drive signal is used to drive the selected transmitter 38 (or group of transmitters 38).

The master unit 34 selectively outputs transmitter drive signals to the data transmission circuit 79 of the transmitter block 26 via a serial bus, such as for example a bidirectional RS-485. In general, the transmitter drive signal is representative of substantially one cycle of a substantially sinusoidally shaped waveform. In one embodiment, the transmitter drive signal has a preselected frequency of about 220 kHz, and the period at which the master unit 34 transmits the transmitter drive signal is about 5 milliseconds.

The transmitter drive signals are received by the data transmission circuit 79 which selectively passes the transmitter drive signals to the transmit circuit 78 to fire selected transmitters 38. Preferably, the data transmission circuit 79 communicates with the transmit circuit 78 via a plurality of signal paths so that the transmitter drive signals can be outputted via the transmit circuit 78 to at least one selected transmitter 38 or group of transmitters 38.

In one preferred embodiment, as shown for example in FIG. 6, the transmit circuit 78 of the transmitter block 26 includes a combination of one bandpass filter 80 (only one being labeled for purposes of clarity) and one driver 84 (only one being labeled for purposes of clarity) for each of the transmitters 38 of the transmitter block 26, so that each transmitter 38 can be controlled independently of the other transmitters 38. In such an embodiment, the bandpass filters 80 are identical and the drivers 84 are identical if the transmitters 38 operate at the same frequency. However, if the transmitters 38 operate at different frequencies, the bandpass filters 80 will be different.

Figure 7A:
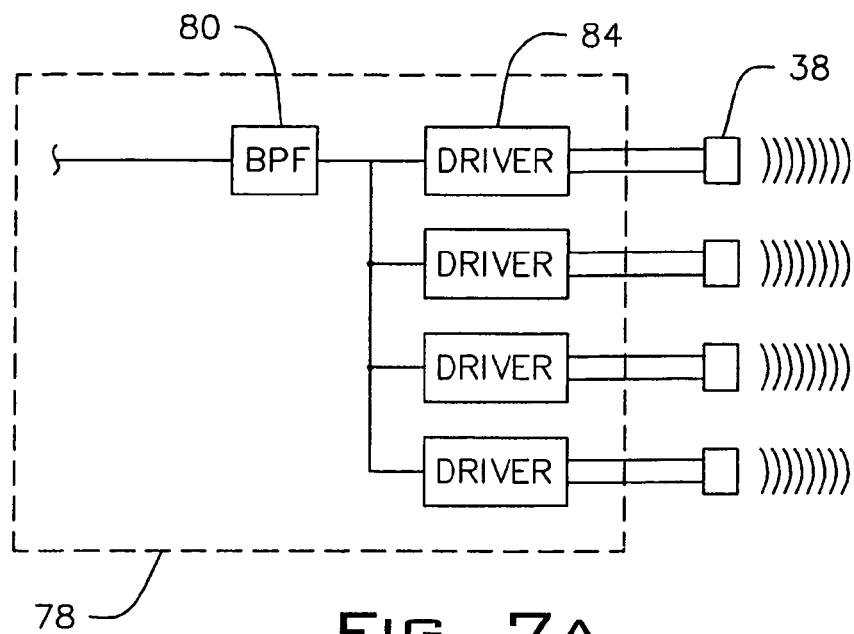
FIG. 7a is a block diagram of one embodiment of a transmit circuit of the transmitter block.
Figure 7B:
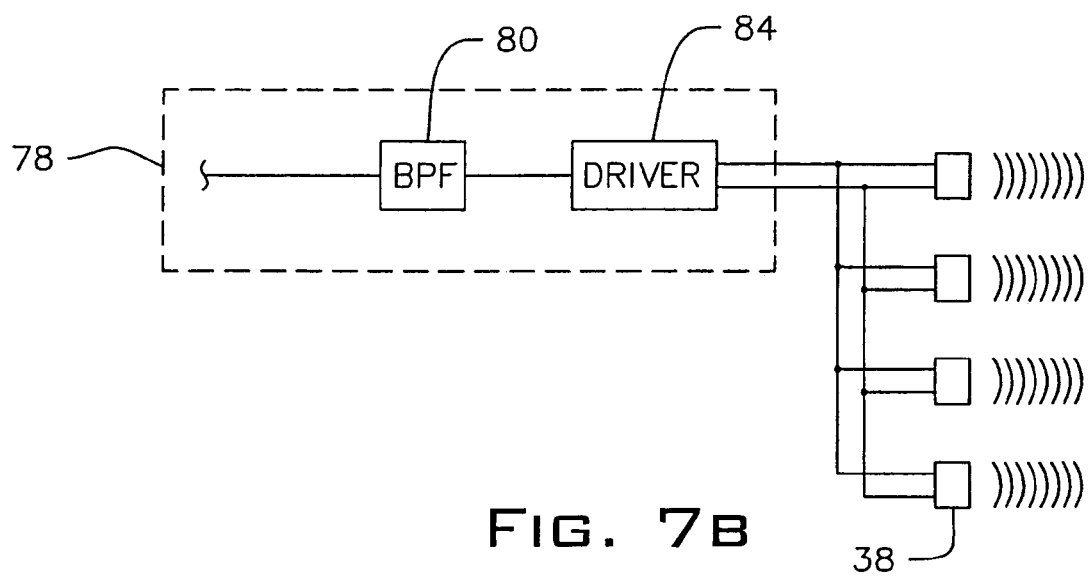
FIG. 7b is a block diagram of another embodiment of a transmit circuit of the transmitter block.

If more than one transmitter 38 operates at the same frequency and are activated at the same time, then the transmitters 38 can also share common components in the transmit circuit 78 to reduce costs and real estate requirements. However, by sharing common components, some flexibility in the setting timing patterns for each transmitter 38 is lost. For example, more than one of the transmitters 38 can share a common bandpass filter 80 and/or driver 84 when operated at the same frequency and/or activated at the same time, such as shown for example in FIGS. 7a-7b. Although the transmitters 38 which share common components are shown in FIGS. 7a-7b as being adjacently disposed, it should be understood that transmitters 38 that share components in the transmit circuit 78 do not have to be adjacently disposed.

For purposes of clarity, the sensor system 10 will be discussed below in further detail with respect to FIG. 6 as having a transmit circuit 78 which includes one bandpass filter 80 and one driver 84 for each transmitter 38 of the transmitter block 26. However, one skilled in the art would understand how to utilize shared components in the transmit circuit 78. Because each transmitter 38, and corresponding bandpass filter 80 and driver 84 operates in a similar manner, for purposes of clarity, only the operation of one transmitter 38 and corresponding bandpass filter 80 and driver 84 is discussed in further detail below.

The bandpass filter 80 is tuned to pass substantially only the selected frequency of the transmitter drive signal and to block substantially all other frequencies, including harmonic frequencies and noise which may result from the transmission of the transmitter drive signal or the noise from a 60-Hz supply voltage, for example. It will be understood by those skilled in the art that bandpass filters, such as the bandpass filter 80, may pass frequencies which are close to the selected frequency upon which the bandpass filter is tuned.

For this reason, the term "substantially only the selected frequency" as used herein is intended to encompass the selected frequency and any frequencies within the range of from about 200 kHz to about 240 kHz (when the selected frequency is about 220 kHz), or preferably within about 6.67 percent (+6.67%) of the selected frequency, although a greater range may be suitable in some applications. Of course, the range of frequencies encompassed by such term may also depend on many factors, such as the type of bandpass filter, and the particular selected frequency.

The bandpass filter 80 receives the transmitter drive signal from the master unit 34 via the data transmission circuit 79, and in response thereto, the bandpass filter 80 conditions the transmitter drive signal to drive the transmitter 38. The conditioned transmitter drive signal will be a substantially sinusoidal waveform. The bandpass filter 80 outputs the conditioned transmitter drive signal to the driver 84. In response thereto, the driver 84 drives the transmitter 38 so as to cause the transmitter 38 to generate ultrasonic signals for the duration of the transmitter drive signal. The at least one driver 84 may be push-pull or single ended with the other terminal of the transmitter 38 connected to ground.

Figure 8:
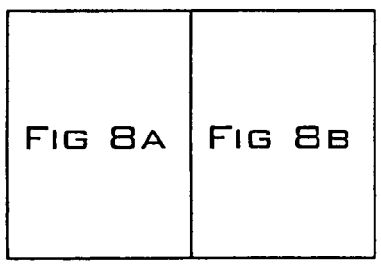
FIG. 8 is a block diagram of one embodiment of a receiver block of the sensor system.
Figure 8A:
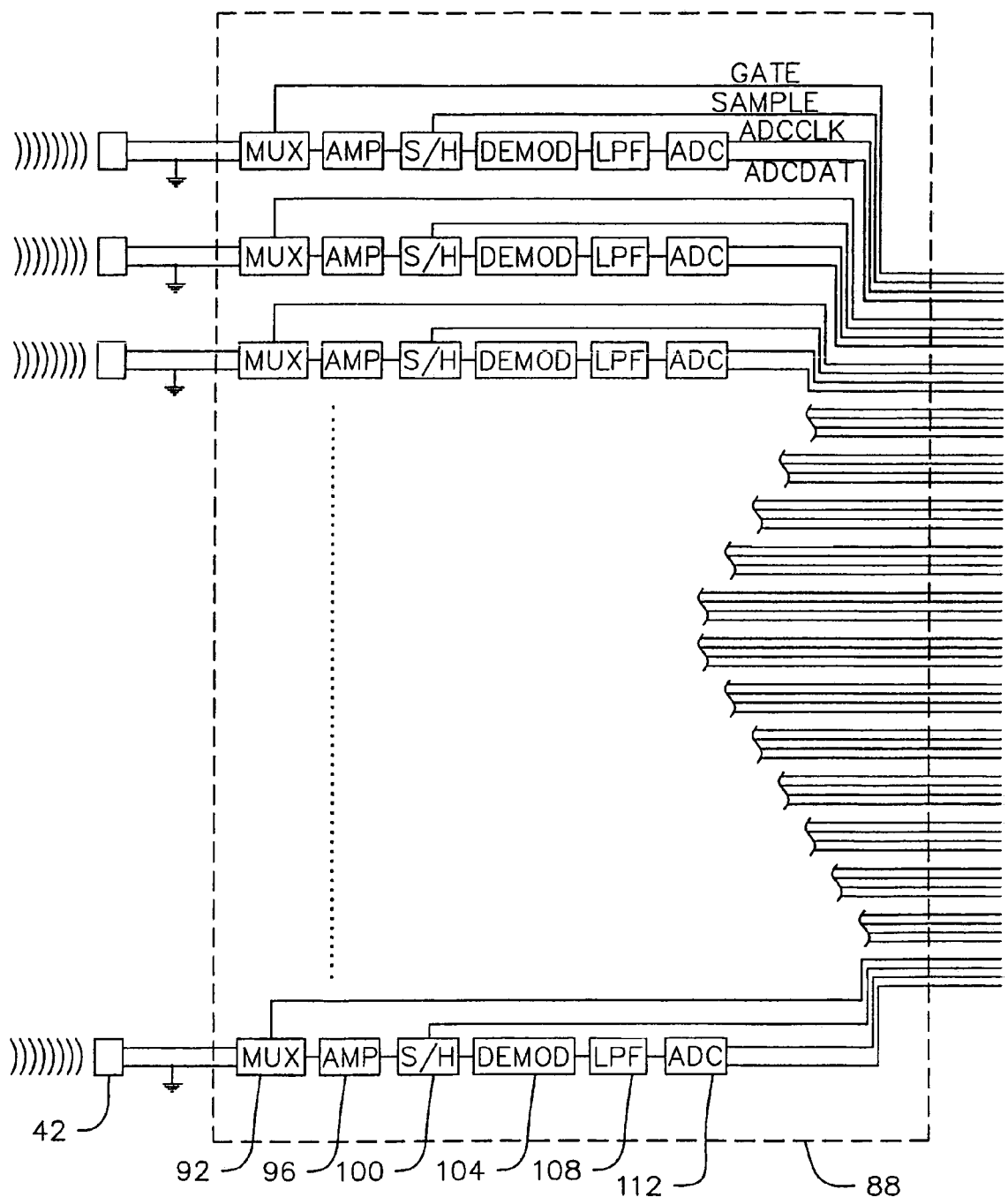
Figure 8B:
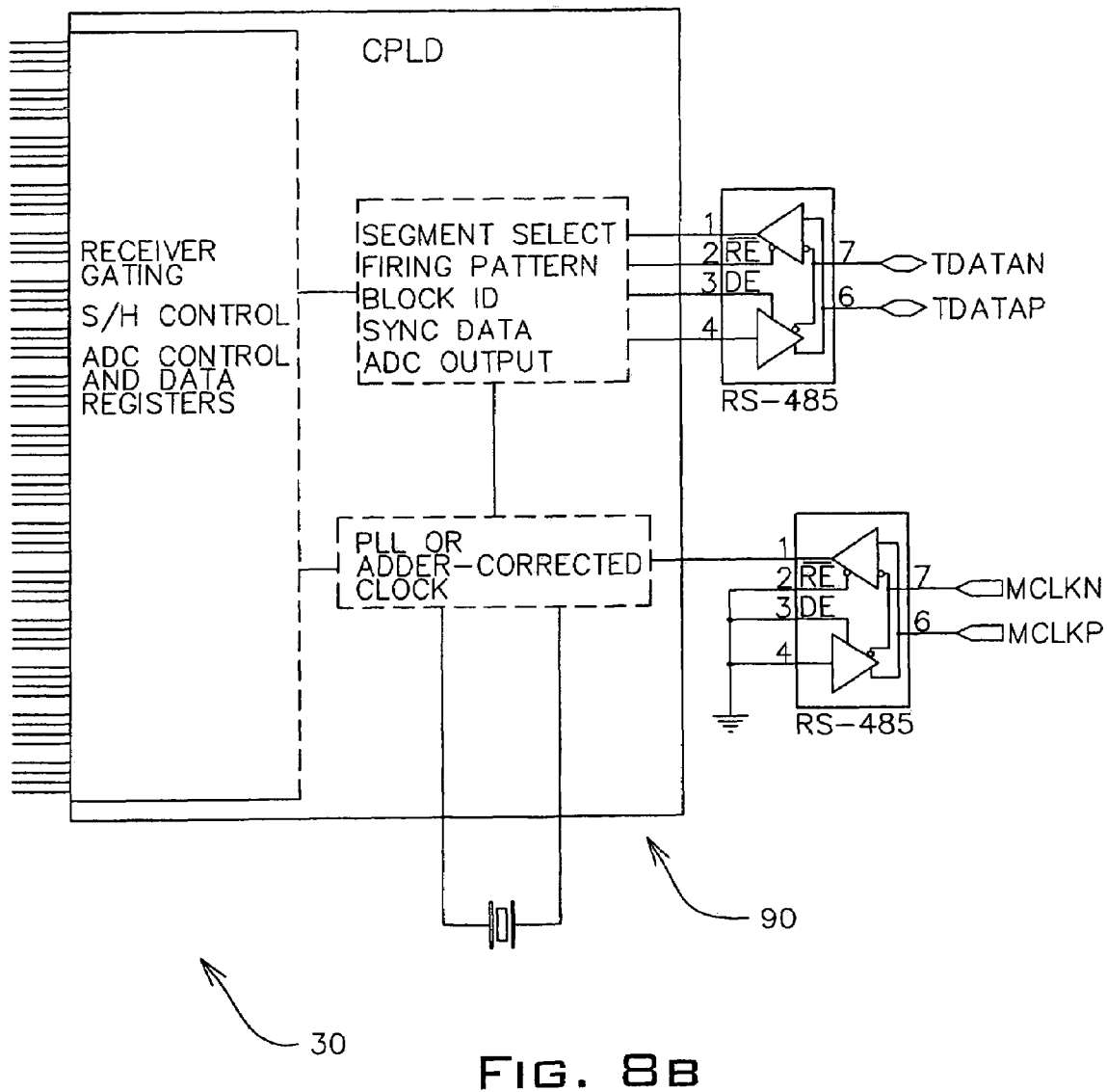

Referring now to FIG. 8, shown therein in block diagram form is one embodiment of one receiver block 30 constructed in accordance with the present invention. The receiver block 30 includes the plurality of receivers 42 (only one being labeled for purposes of clarity), wherein each receiver 42 is selectively capable of receiving ultrasonic signals in response to the receiver cutoff signal outputted by the master unit 34 to the receiver 42. Although the receiver block 26 is shown in FIG. 8 as including sixteen receivers 42, it should be understood that the receiver block 30 can have any number of receivers 42.

In one preferred embodiment, the receiver block 30 further includes a receive circuit 88 and a data transmission circuit 90 to exchange data between the master unit 34 and the plurality of receivers 42. In general, the receive circuit 88 and the data transmission circuit 90 cooperate with the master unit 34 to set and synchronize timing patterns for the receivers 42, to turn on and off the receivers 42, to receive the receiver output signals from the receivers 42, and to identify or diagnose the receiver block 26. More particularly, the data transmission circuit 90, which can be for example a complex programmable logic device (CPLD), cooperates with the master unit 34 to control which receiver 42 (or group of receivers 42) receives the receiver cutoff signal. The receive circuit 90 toggles the selected receiver 42 (or group of receivers 42) in response to the receiver cutoff signal outputted by the master unit 34 via the data transmission circuit 90, and smooths and amplifies the receiver output signals generated by the selected receiver 42 (or group of receivers 42).

The master unit 34 selectively outputs receiver cutoff signals to the data transmission circuit 90 of the receiver block 30 via a serial bus, such as for example a bidirectional RS-485. The receiver cutoff signals are received by the data transmission circuit 90 which selectively passes the receiver cutoff signals to the receive circuit 88 to toggle the selected receivers 42. The master unit 34 also receives the receiver output signals generated by the selected receivers 42 via the receive circuit 88 and data transmission circuit 90. The data transmission circuit 90 communicates with the receive circuit 88 via a plurality of signal paths so that the receiver cutoff signals can be outputted to at least one selected receiver 42 or group of receivers 42, and the receiver output signals can be outputted from each receiver 42 to the data transmission circuit 90.

Figure 9A:
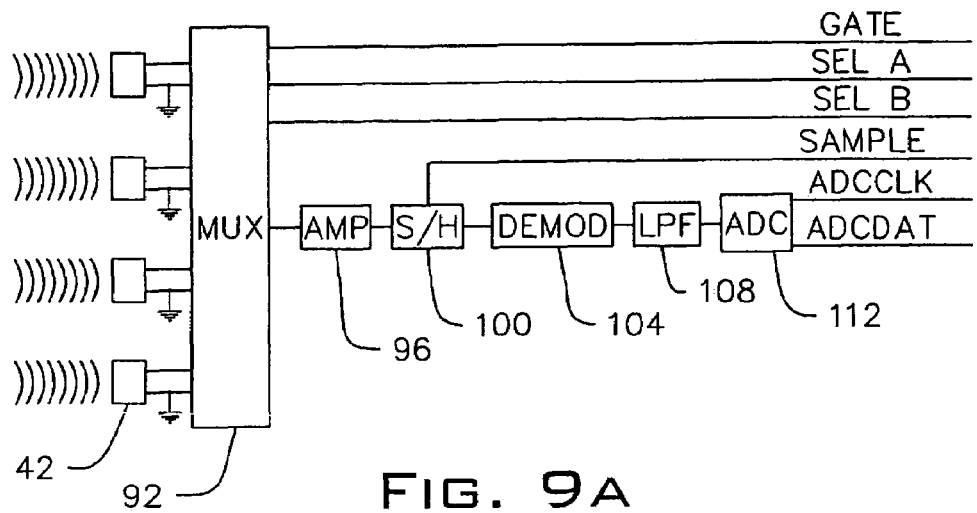
FIG. 9a is a block diagram of one embodiment of a receive circuit of the receiver block.
Figure 9B:
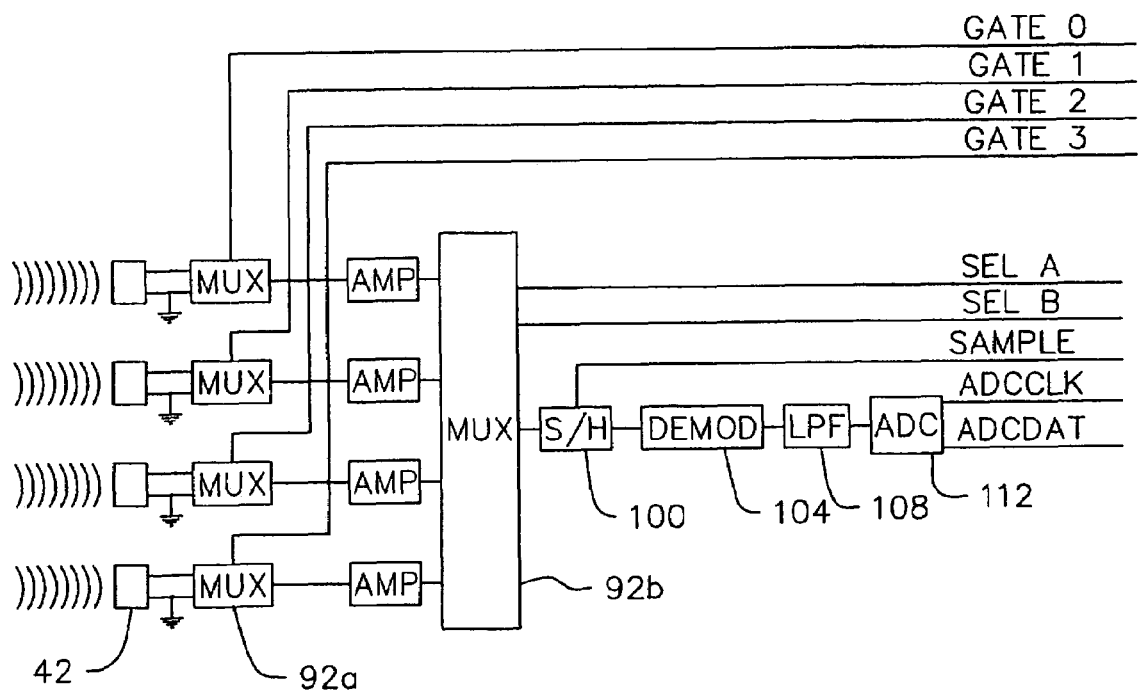
FIG. 9b is a block diagram of another embodiment of the receive circuit of the receiver block.
Figure 9C:
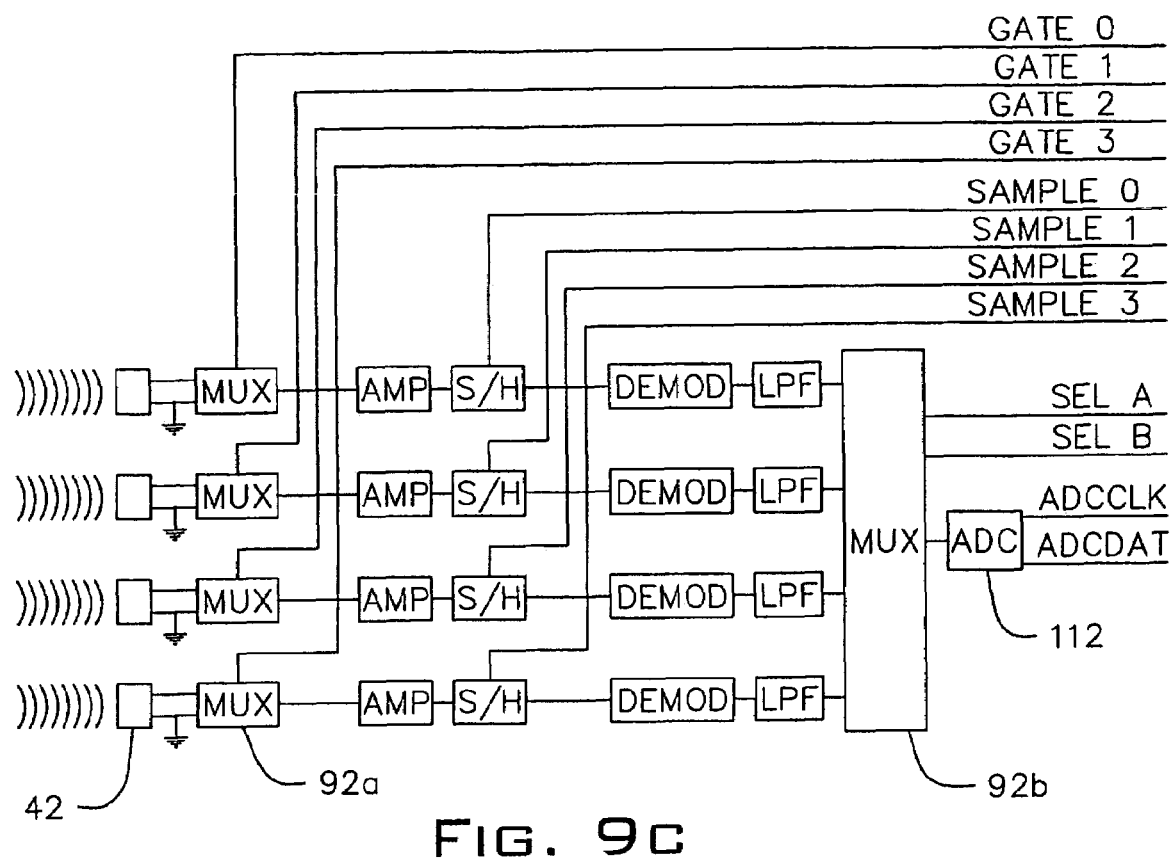
FIG. 9c is a block diagram of another embodiment of the receive circuit of the receiver block.

In one preferred embodiment, as shown for example in FIG. 8, the receive circuit 88 of the receiver block 30 includes a combination of one multiplexer 92, one amplifier 96, one sample and hold 100, one demodulator 104, one lowpass filter 108, and one analog-to-digital converter 112 (only one of each being labeled for purposes of clarity) for each of the receivers 42 of the at least one receiver block 30. However, more than one of the receivers 42 can also share components in the receiver block 30 to reduce costs and real estate requirements. For example, more than one of the receivers 42 can share a common multiplexer 92, amplifier 96, sample and hold 100, demodulator 104, lowpass filter 108, and analog-to-digital converter 112 if the associated receivers 42 operate at a similar frequency range, such as shown for example in FIG. 9a. For more flexibility however, multiple multiplexers 92 can be utilized. For example, more than one of the receivers 42 can share a common sample and hold 100, demodulator 104, lowpass filter 108, and analog-to-digital converter 112 with use of an additional multiplexer 92b receiving the amplified receiver output signals from associated receivers 42 operating at similar frequency ranges, such as shown for example in FIG. 9b. In another example, more than one receiver 42 can share a common analog-to-digital converter 112 with the use of the additional multiplexer 92b receiving the filtered receiver signals from associated receivers 42, such as shown for example in FIG. 9c. Such an embodiment would allow data acquisition from only one of the combined channels at a time, but individual frequencies, gatings, and sample-and-hold timings could be utilized. If each receiver 42 has a dedicated analog-to-digital converter 112, simultaneous acquisition of data from any combination of receivers 42 at any time is possible. Further, greater flexibility with respect to transmitter firing patterns or multiple frequencies is also possible.

For purposes of clarity, the sensor system 10 will be discussed below in further detail with respect to FIG. 8 as having a receive circuit 88 which includes one multiplexer 92, amplifier 96, sample and hold 100, demodulator 104, lowpass filter 108, and analog-to-digital converter 112 for each receiver 42 of the at least one receiver block 30. However, one skilled in the art would understand how to utilize shared components in the receive circuit 88. Because each receiver 42 and corresponding multiplexer 92, amplifier 96, sample and hold 100, demodulator 104, lowpass filter 108, and analog-to-digital converter 112 operates in a similar manner, for purposes of clarity, only the operation of one receiver 42 and corresponding multiplexer 92, amplifier 96, sample and hold 100, demodulator 104, lowpass filter 108, and analog-to-digital converter 112 is discussed in further detail below.

When toggled on, the receiver 42 generates a receiver output signal in response to the receipt of ultrasonic signals. To toggle the receiver 42, the receiver cutoff signal is outputted by the master unit 34 and passed by the data transmission circuit 90 to the receive circuit 88. The corresponding multiplexer 92 of the receive circuit 88 toggles the receiver 42 so that the receiver 42 is permitted to receive ultrasonic signals for the duration of the receive cutoff signal outputted by the master unit 34. In one embodiment, to toggle the receiver 42, the multiplexer 92 selectively clamps the positive and negative terminals of the receiver 42 to ground. For example, the receiver 42 can be turned "off" by the receiver cutoff signal in the second mode by clamping the positive terminal of the receiver 42 to ground.

By toggling the receiver 42 between the first mode and the second mode, the receiver 42 is only permitted to generate the receiver output signals during each period for the predetermined time after the transmitter drive signal has been transmitted to the corresponding transmitter 38. The receiver cutoff signal is generally sent to the receiver 42 in synchronization with the transmitter drive signal sent to the corresponding transmitter 38. By synchronizing the transmitter drive signal and the receiver cutoff signal for the paired transmitter 38 and receiver 42, interference between different pairs of transmitters 38 and receivers 42, as well as other noise, can be reduced.

The predetermined time that the receiver 42 is permitted to generate the receiver output signal is tuned for a period so as to permit the ultrasonic signals to be transmitted by the transmitter 38 across the sensing gap 58 of the sensor field of view 46 and thereby received by the receiver 42. The predetermined time that the receiver 42 is permitted to generate the receiver output signal is tuned for a period to also prevent any noise caused by the reception of the ultrasonic signals transmitted by non-corresponding transmitters 38. Thus, it can be seen that the predetermined time will be determined by: (1) the frequency of the transmitter drive signal; and (2) the sensing gap 58 of the of the sensor field of view 46. Given a transmitter drive signal of about 220 kHz, and a sensing gap 58 of about one inch, a predetermined time period between about 100 microseconds to about 195 microseconds has been found to be appropriate, depending on the amount of time that passes between the start of the transmitter drive signal and the start of the receiver cutoff signal.

When the receiver 42 is toggled on and receives ultrasonic signals, the receiver 42 generates a receiver output signal indicative of the ultrasonic signals received, which is outputted to the multiplexer 92. The multiplexer 92 passes the receiver output signal received to the amplifier 96 which amplifies the receiver output signal. The amplified receiver output signal is passed to the sample and hold 100. The sample and hold 100 acts as a spike remover which removes all voltage spikes from the amplified receiver output signal. The stripped, amplified receiver output signal is then passed to the demodulator 104. The demodulated receiver output signal is passed by the demodulator 104 to the lowpass filter 108, which smooths the receiver output signal. The filtered receiver output signal is then passed to the analog-to-digital converter 112 so as to form a DC signal which is outputted to the master unit 34 via the data transmission circuit 90 so that the receiver output signal can be utilized by the master unit 34 to generate the sensor output signals (as discussed above).

In one embodiment, the data transmission circuit 90 preferably has dedicated hardware logic that are adapted for time-critical functions such as gating and controlling the sample-and-holds 100, which are generally synchronized to the firing of corresponding transmitters 38. The data transmission circuit 90 is synchronized utilizing the master clock of the control circuit 68 of the master unit 34. Further, the receiver block 30 can include a microcontroller (not shown) which cooperates with the data transmission circuit 90 to handle data communications, to control the analog-to-digital converters 112, or to perform data acquisitions via on-chip analog-to-digital functions.

As discussed above, in one embodiment of the present invention, the master unit 34 controls the firing sequence and/or frequency of the transmitters 38 so that each transmitter 38 (or group of transmitters 38) transmits ultrasonic signals at a different time and/or frequency than adjacently disposed transmitters 38 (or groups of transmitters 38). The master unit 34 also controls the reception sequence of the receivers 42 so that each receiver 42 (or group of receivers 42) receives ultrasonic signals at a different time than adjacently disposed receivers 42 (or groups of receivers 42), generally in accordance with the firing sequence of corresponding transmitters 38. The timing pattern in which each of the plurality of transmitters 38 is "fired", i.e. caused to transmit ultrasonic signals, will depend on the relative physical arrangement of the transmitters 38. Also, the timing pattern in which each of the plurality of receivers 42 is toggled "on", i.e. permitted to generate receiver output signals responsive to the receiver 42 receiving ultrasonic signals, will depend on the relative physical arrangement of the receivers 42.

The distance between each transmitter 38 and corresponding receiver 42 will also have different signal travel timing relationships and therefore may require different transmitter and receiver timing patterns. The frequency relationship between adjacent or nearby transmitters 38 (and corresponding receivers 42) will also effect timing patterns since different operating frequencies will allow for more simultaneous transmission (and reception) of ultrasonic signals of adjacent or nearby transmitters 38 (and corresponding receivers 42). Another factor that may affect timing patterns include the desired rate at which receiver output signals from one or more receivers 42 is to be evaluated so that the corresponding sensing area in the sensor system 10 is updated during real-time sensing.

In general, a master clock of the control circuit 68 of the master unit 34 is utilized in the synchronization of timing patterns. In one embodiment, such synchronization can be implemented using IEEE 1588 Precision Time Protocol techniques. Utilizing such a synchronization technique allows for the timing pattern of each transmitter 38 of the at least one transmitter block 26 and each receiver 42 of the at least one receiver block 30 to be arranged so that interference between the transmission and reception of ultrasonic signals between transmitters 38 and receivers 42 of the same or different transmitter blocks 26 and receiver blocks 30, respectively, are substantially reduced.

Further, because the timing patterns and/or frequencies of adjacent or nearby transmitters 38 (and corresponding receivers 42) in the staggered matrix formation are preferably arranged such that adjacent or nearby transmitters 38 generate (and receivers 42 receive) ultrasonic signals at different times or frequencies, there will be minimal or no overlap or interference between ultrasonic signals transmitted by adjacent or nearby transmitters 38 or received by adjacent or nearby receivers 42. However, any overlap which occurs can be compensated for using techniques known in the art.

It can be seen that the receiver output signals from receivers 42 which are completely blocked or unblocked by the at least one web material 14 is less relevant because they indicate less information about the position of at least one edge 12 of the at least one web material 14. For efficiency, these output signals produced by the receivers 42 which are completely blocked or unblocked may be ignored or the corresponding transmitter 32 and/or receiver 42 may be powered off until such time as the at least one web material 14 moves and the corresponding transmitter 38 and/or receiver 42 is powered back on. As such, the present invention contemplates that the master unit 34 of the sensor system 10 can selectively actuate and deactuate each of the transmitters 38 and/or receivers 42 so as to reduce power consumption and processing capacity of the sensor system 10. The actuation and deactuation of the transmitters 38 and/or receivers 42 generally depends on the relative position of the at least one edge 12 of the at least one web material 14 being sensed, similar to the method described for example in U.S. Pat. No. 6,323,948, entitled "Light Sensor for Web-Guiding Apparatus", the contents of which are hereby expressly incorporated herein.

In one embodiment, the transmitters 38 and/or receivers 42 within a predetermined range of the position of the at least one edge 12 of the at least one web material 14 are actuated, and the transmitters 38 and/or receivers 42 outside the range are deactuated. Such logical web edge sensing of the present invention is especially useful in that it requires no mechanical movement for the sensor system to "follow" the at least one edge 12 of the at least one web material 14. In one embodiment, the transmitters 38 and/or receivers 42 within a predetermined range of the at least one web material 14 can be further categorized in a primary edge detection range and a secondary edge detection range so as to more accurately detect the direction of movement and follow the at least one edge 12 of the at least one web material 14.

Another advantage of such selective sensing is that by operating only certain portions of the sensor system 10 (i.e., the transmitters 38 and/or receivers 42 within the predetermined range of the position of the at least one edge 12 of the at least one web material 14) is the reduction of noise that may arise from generating ultrasonic signals which are not necessary for sensing the at least one edge 12 of the at least one web material 14. Further efficiency arises since only a portion of the entire system capability is used for detecting the at least one edge 12 of the at least one web material 14 during normal operation.

Figure 10A:
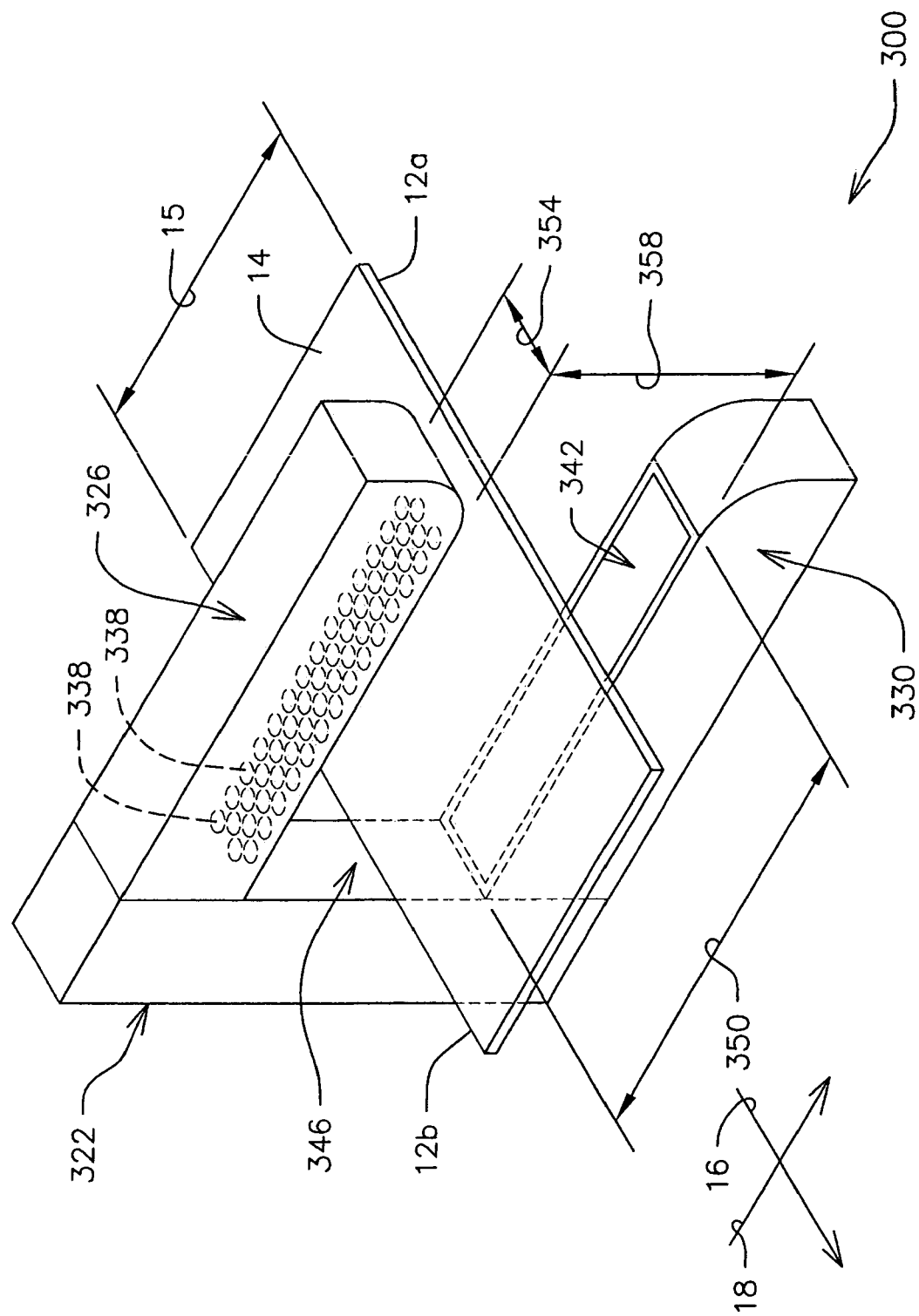
FIG. 10a is a perspective, diagrammatic view of one embodiment of a sensor system constructed for reflective operation in accordance with the present invention (wherein one web material is being sensed).
Figure 11:
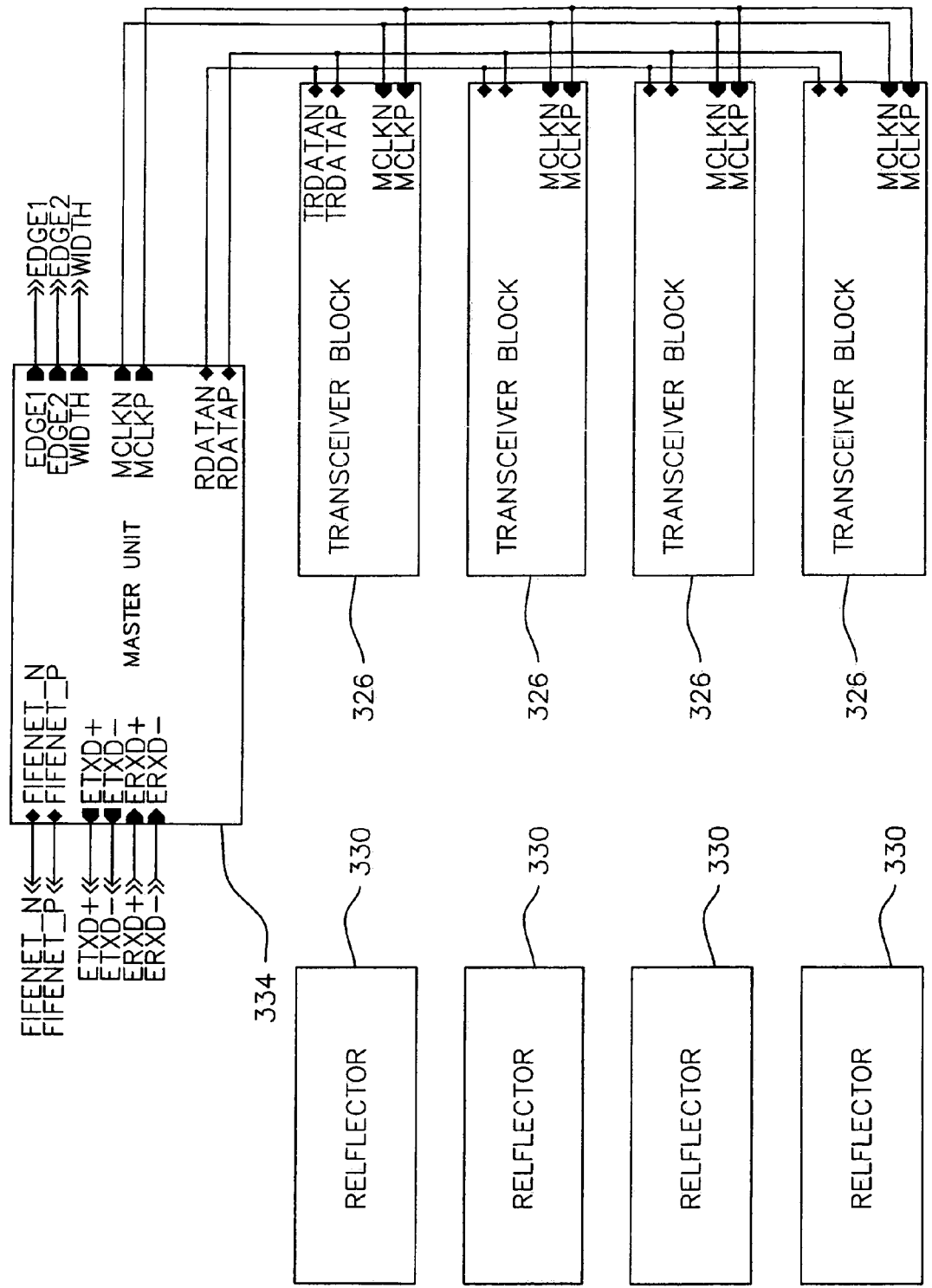
FIG. 11 is a block diagram of one embodiment of a sensor system for reflective operation constructed in accordance with the present invention.

Referring now to FIG. 10a, shown therein is a sensor system 300 constructed in accordance with the present invention. The sensor system 300 is constructed for reflective operation. The sensor system 300 includes a housing 322 which is adapted to receive at least one transceiver block 326 and at least one reflector 330. As best shown in FIG. 11, the sensor system 300 can include more than one transceiver block 326. Although the sensor system 300 is shown in FIG. 11 as having four transceiver blocks 326, it should be understood that the sensor system 300 can have any number of transceiver blocks 326. Preferably, the sensor system 300 includes the same number of reflectors 330 as there are transceiver blocks 326 in the sensor system 300 so that each reflector 330 can be paired with a corresponding transceiver block 326. However, it should be understood that the present invention contemplates that more than one transceiver block 326 can be paired or grouped with one reflector 330, and more than one reflector 330 can be paired or grouped with one transceiver block 326. For example, one continuous reflector 330 can be paired with two or more transceiver blocks 329.

The at least one transceiver block 326 of the sensor system 300 includes a plurality of transceivers 338 (shown in phantom, only two being labeled in FIG. 10a for purposes of clarity). Each transceiver 338 is selectively capable of generating ultrasonic signals, and each transceiver 338 is further capable of selectively receiving ultrasonic signals and generating a receiver output signal indicative of the ultrasonic signals received. The at least one reflector 330 includes a reflective material 342 capable of reflecting at least a portion of the ultrasonic signals generated by the plurality of transceivers 338. The reflective material 342 can be for example a metal, such as aluminum.

The sensor system 300 operates in a similar manner to the sensor system 10, except that the functions of the at least one transmitter block 26 and the at least one receiver block 30 of the sensor system 10 are essentially performed by the at least one transceiver block 326 of the sensor system 300 since the plurality of transceivers 338 of the transceiver block 326 are capable of transmitting and receiving ultrasonic signals.

As shown in FIG. 10a, the housing 322 is preferably mounted perpendicularly with respect to the web direction of travel 16, and the at least one transceiver block 326 and the at least one reflector 330 are on opposite sides of the at least one web material 14 and are disposed such that the ultrasonic signals transmitted by the plurality of transceivers 338 of the at least one transceiver block 326 are substantially projected on to the reflective material 342 of the at least one reflector 330 and reflected substantially back to the plurality of transceivers 338.

The housing 322 serves to space the at least one transceiver block 326 from the at least one reflector 330 to form a sensor field of view 346 therebetween. The sensor field of view 346 has a length 350, a width 354, and a sensing gap 358. Preferably, the length 350 of the sensor field of view 346 is greater then the width 15 of the at least one web material 14. However, the length 350 of the sensor field of view 346 can be less than the width 15 of the at least one web material 14, such as for example when only one edge 12 of the at least one web material 14 is being sensed. The sensing gap 358 of the sensor field of view 346 extends generally in between the at least one transceiver block 326 and the at least one reflector 330, and is sufficient to dispose the at least one web material 14 therebetween.

Although the sensor field of view 346 is preferably continuous, it should be understood that the sensor field of view 346 can also be discontinuous. For example, when the sensor system 300 has more than one transceiver block 326 and/or more than one reflector 330, the transceiver blocks 326 and/or reflectors 330 can be staggered or disposed remotely from each other.

In general, as the at least one web material 14 travels through at least a portion of the sensor field of view 346, the at least one web material 14 will interfere with or block the passage of at least a portion of the ultrasonic signals transmitted by the plurality of transceivers 338 of the at least one transmitter block 326 and reflected by the at least one reflector 330 because the ultrasonic signals, upon reaching the at least one web of material 14, are partially absorbed, reflected, or deflected by the at least one web material 14. Thus, the ultrasonic signals received by each transceiver 338 will depend on the relative location of the at least one web material 14 to the transceiver 338. As such, and as will be understood by those skilled in the art, the ultrasonic signals received by the transceivers 338 of the at least one transceiver block 330 are indicative of the position of at least one edge 12 of the at least one web material 14, as well as other information which can be determined therefrom, such as the center position of the at least one web material 14 and transitions between two or more web materials 14. Further, with real-time sensing, deviations of the at least one web material 14 in the direction 18 can be detected as the at least one web material 14 moves through at least a portion of the sensor field of view 346.

Each of the transceivers 338 of the at least one transceiver block 326 can be any transducer capable of generating ultrasonic signals in response to the receipt of electrical signals, and generating electrical signals in response to the receipt of ultrasonic signals. For example, each of the transceivers 338 can be an ultrasonic transceiver capable operating in transmitter mode or receiver mode. In one embodiment, each of the transceivers 38 can be a MA200D1 High-Frequency Ultrasonic Sensor, having an operating frequency range from about 220 kHz±about 20 kHz, available from Murata Manufacturing Co., Ltd. of Japan. However, it should be understood that each of the transceivers 338 can operate in another frequency range. For example, a frequency range can be selected so as to eliminate interference from expected environmental sound waves (e.g. from machinery or other nearby sensor systems). Also, the plurality of transceivers 338 do not have to operate at the same frequency. For example, each transceiver 338 can have a different operating frequency than an adjacently or nearly disposed transceiver 338 in the same transceiver block 326 or in another adjacently disposed transceiver block 326 so as to help reduce interference between ultrasonic signals generated by two or more transceivers 38.

Preferably, each transceiver 338 of the at least one transceiver block 326 is a discrete unit that can be independently disposed in and supported by the housing 322, and has its own sound conducting material. As such, it should be understood that each transceiver 338 of the at least one transceiver block 326 can be isolated from the other transceivers 338 and disposed on a different plane. Further, the at least one transceiver block 326 may also include sound insulation material 359 (such as shown for example in FIG. 12a), such as for example rubber or foam material, disposed substantially around a portion of each of the transceivers 338 so as to insulate the transceivers 338 from undesired signals and vibrations (e.g. from the housing 322) while allowing the transceivers 338 to transmit ultrasonic signals to the reflective material 342 of the at least one reflector 330. In one preferred embodiment, the sound insulation material 359 is disposed around a portion of each of the transceivers 338 such that each transceiver 338 remains independent and thus further insulated from adjacently disposed transceivers 338 in the at least one transceiver block 326.

In one preferred embodiment, the transceivers 338 have a symmetric circular shape, such as shown for example in FIG. 10a. However, it should be understood that the transmitters 38 can have any shape, and can be either symmetric or asymmetric, generally depending on the desired beam profile of the produced ultrasonic signals. For example, as shown in FIG. 10c, the transceivers 338 may have an asymmetric rectangular shape.

Figure 12A:
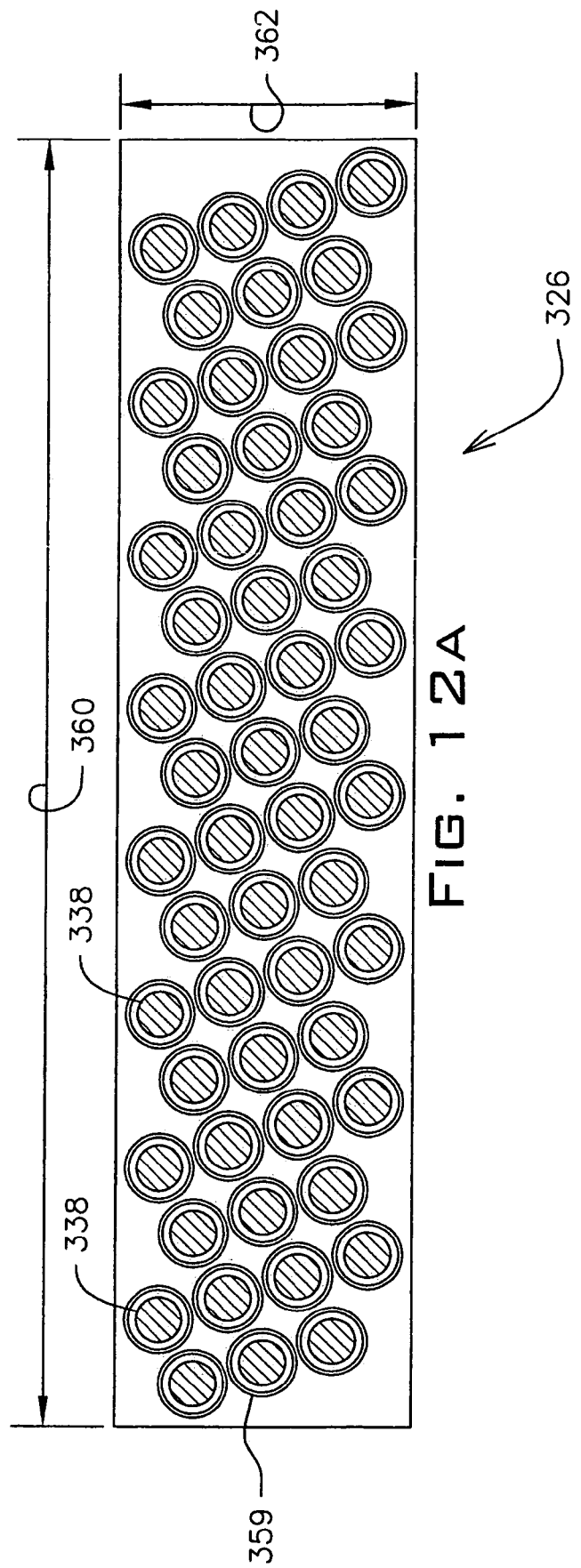
FIG. 12a is an elevational, diagrammatic view of one embodiment of a transceiver block of the sensor system.

In one embodiment, the plurality of transceivers 338 are arranged in the at least one transmitter block 26 in a staggered matrix formation, as shown best in FIG. 12a. In the staggered matrix formation, the transceivers 338 are disposed in staggered rows, whereby each transceiver 338 in the rows effectively increases a length 360 of the at least one transceiver block 26 and each staggered row effectively increases a width 362 of the at least one transceiver block 326. Although the at least one transceiver block 326 is shown in FIG. 12a as having seven staggered rows of transceivers 338, with each row having eight transceivers 338, it should be understood that the at least one transceiver block 326 may have any number of transceivers 338 in each row of the staggered matrix formation, and the at least one transceiver block 326 can have any number of rows of transceivers 338. Further, each row may have the same or a different number of transceivers 338 as an adjacently disposed row of transceivers 338.

Similar to the plurality of transmitters 38 and receivers 42 of the sensor system 10, placing the transceivers 338 of the sensor system 300 in a staggered arrangement effectively reduces gaps or spaces where there is an absence of ultrasonic signals transmitted and received by the plurality of transceivers 338 of the at least one transceiver block 326 across at least one of the length 350 or the width 354 of the sensor field of view 346, through which at least a portion of the at least one web material 14 passes and is being sensed, thereby providing a more continuous sensor field of view 346 of the sensor system 300 during real-time sensing of the at least one web material 14. As with sensor system 10, the more continuous field of view 346 of sensor system 300 provides more flexibility in the positioning and/or alignment of the at least one web material 14 in the sensor field of view 346 of the sensor system 300.

Preferably, the transceivers 338 of the at least one transceiver block 326 are positioned near to adjacently disposed transceivers 38 so to decrease the distance between adjacently disposed transmitters while still allowing for mounting and support by the housing 322 for the transceivers 338, and if desired, the insulating material 359. In one preferred embodiment, each transceiver 338 is arranged in the staggered matrix formation such that at least one edge of a proportional band area of the transceiver 338 is substantially aligned with at least one edge of a proportional band area of an adjacently disposed transceivers 338 and/or at least one edge of a proportional band area of another transceiver 338 along the length 360 of the transceiver block 326 such that gaps along the overall sensing length 360 of the transceiver block 326 are essentially reduced. Preferably, the edges of the proportional band areas are aligned such that the proportional band areas overlap. Overlapping helps to remove gaps and to compensate for such other factors as manufacturing tolerance allowances of other elements of the sensor system 300, such as for example the housing 322 and transceivers 338. Therefore, in such an embodiment, the positioning of the transceivers 338 will generally depend on the physical shape, dimensions, and proportional band area of each of the transceivers 338. In one embodiment, the proportional band area of each transceiver 338 is defined by the 10%-90% near-linear performance of the transceiver 338. However, other limits and/or considerations may be used to define the proportional band area of each of the transceivers 338.

Figure 12B:
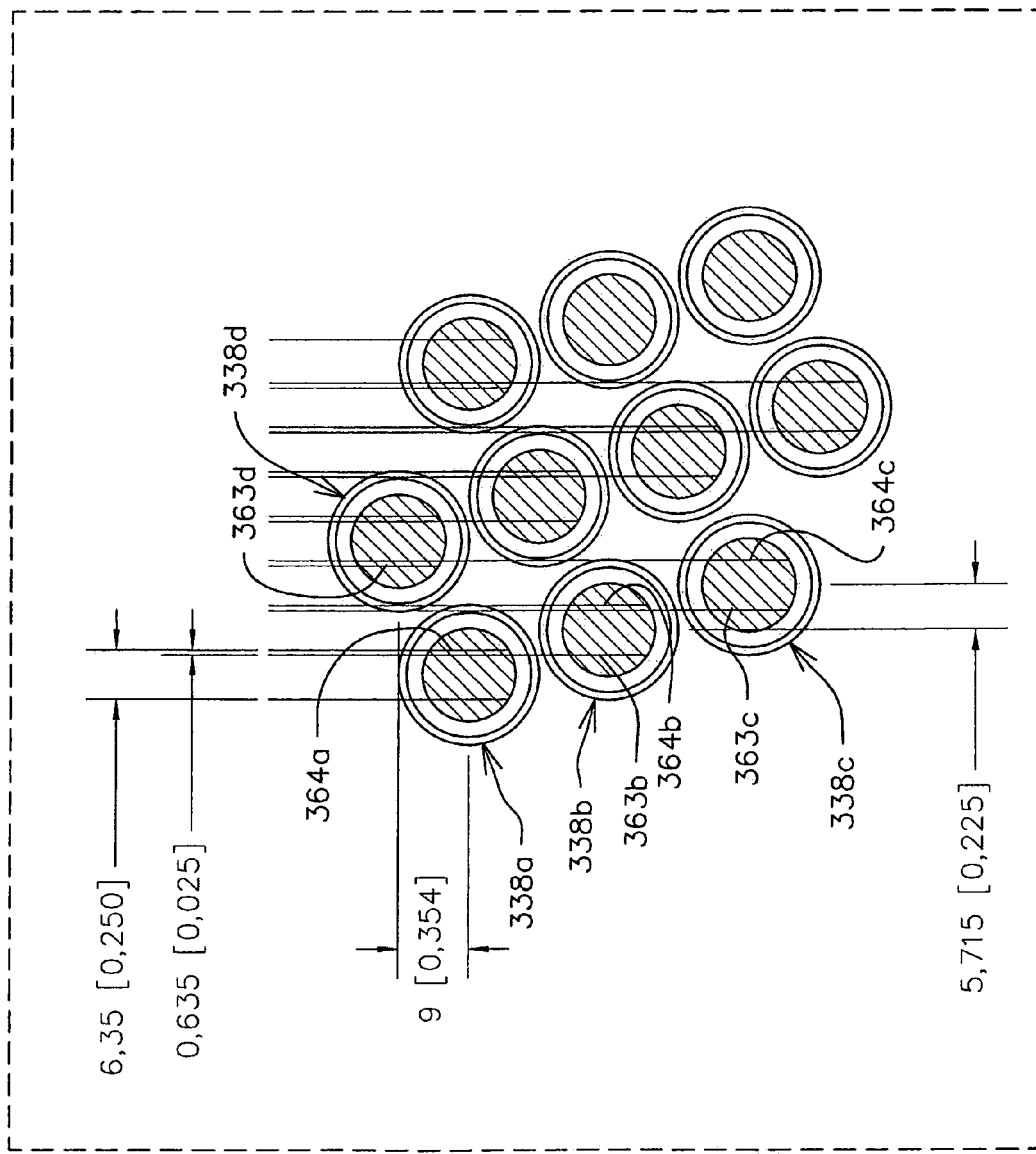
Figure 13B:
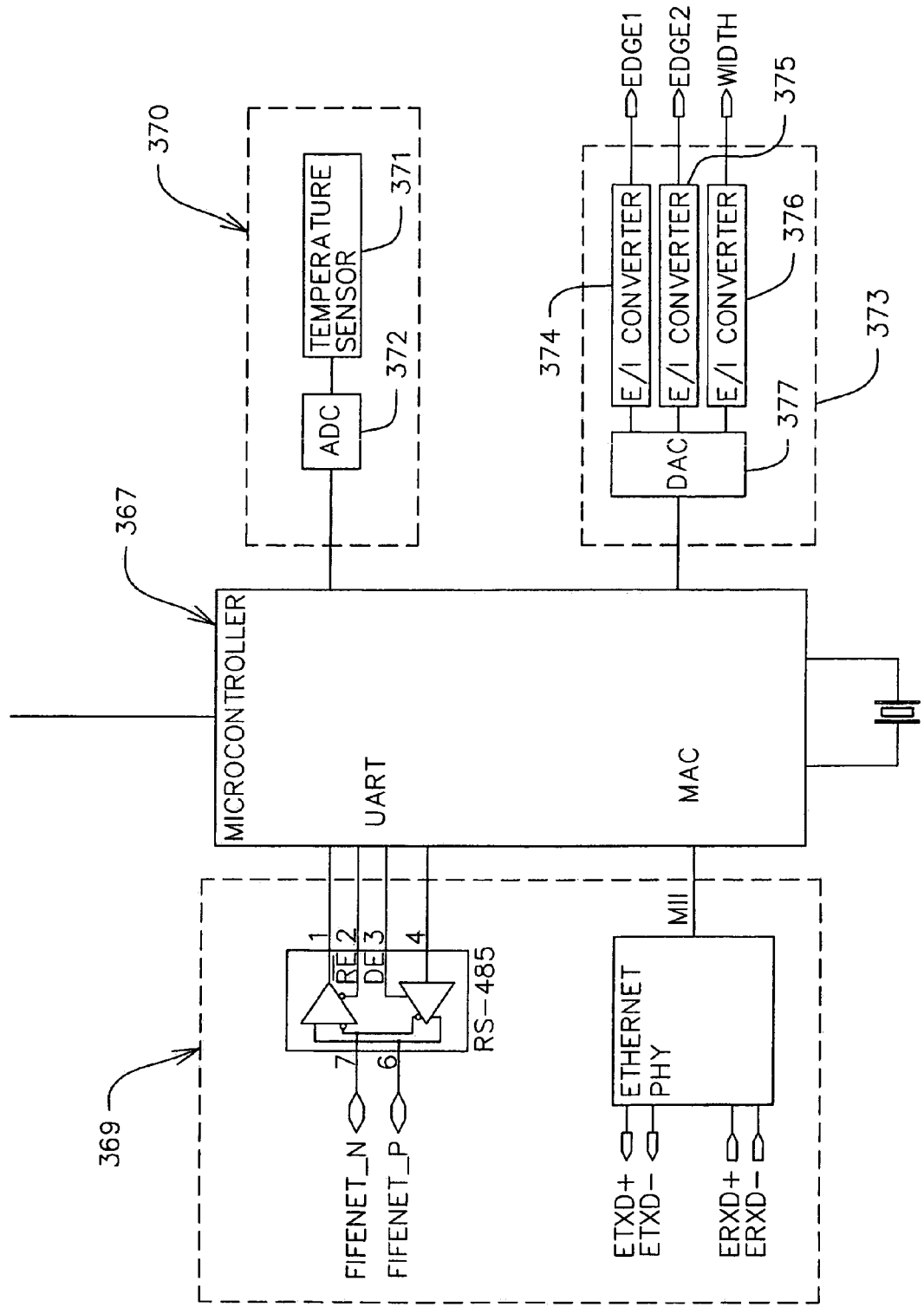
Figure 14A:
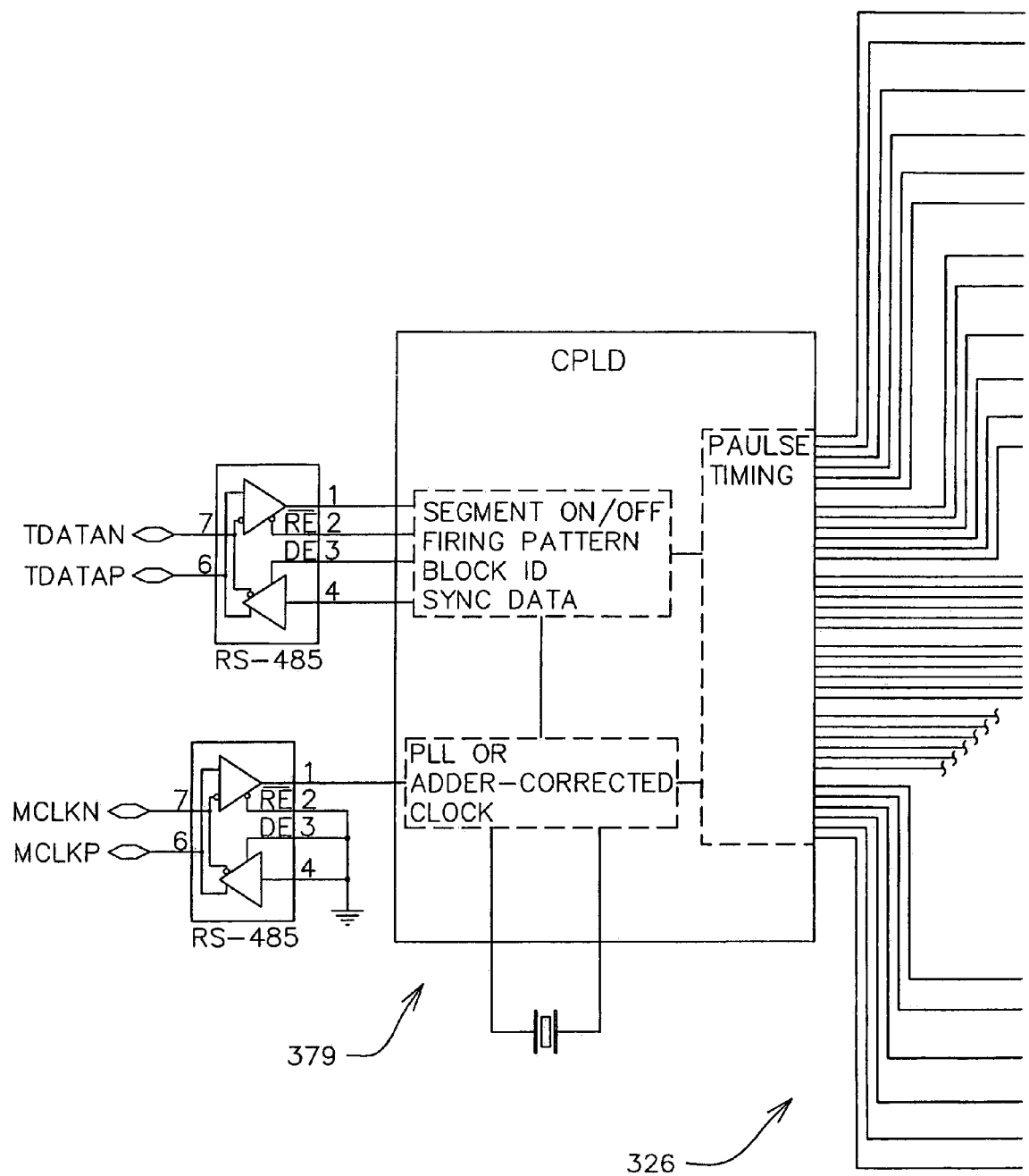
Figure 14B:
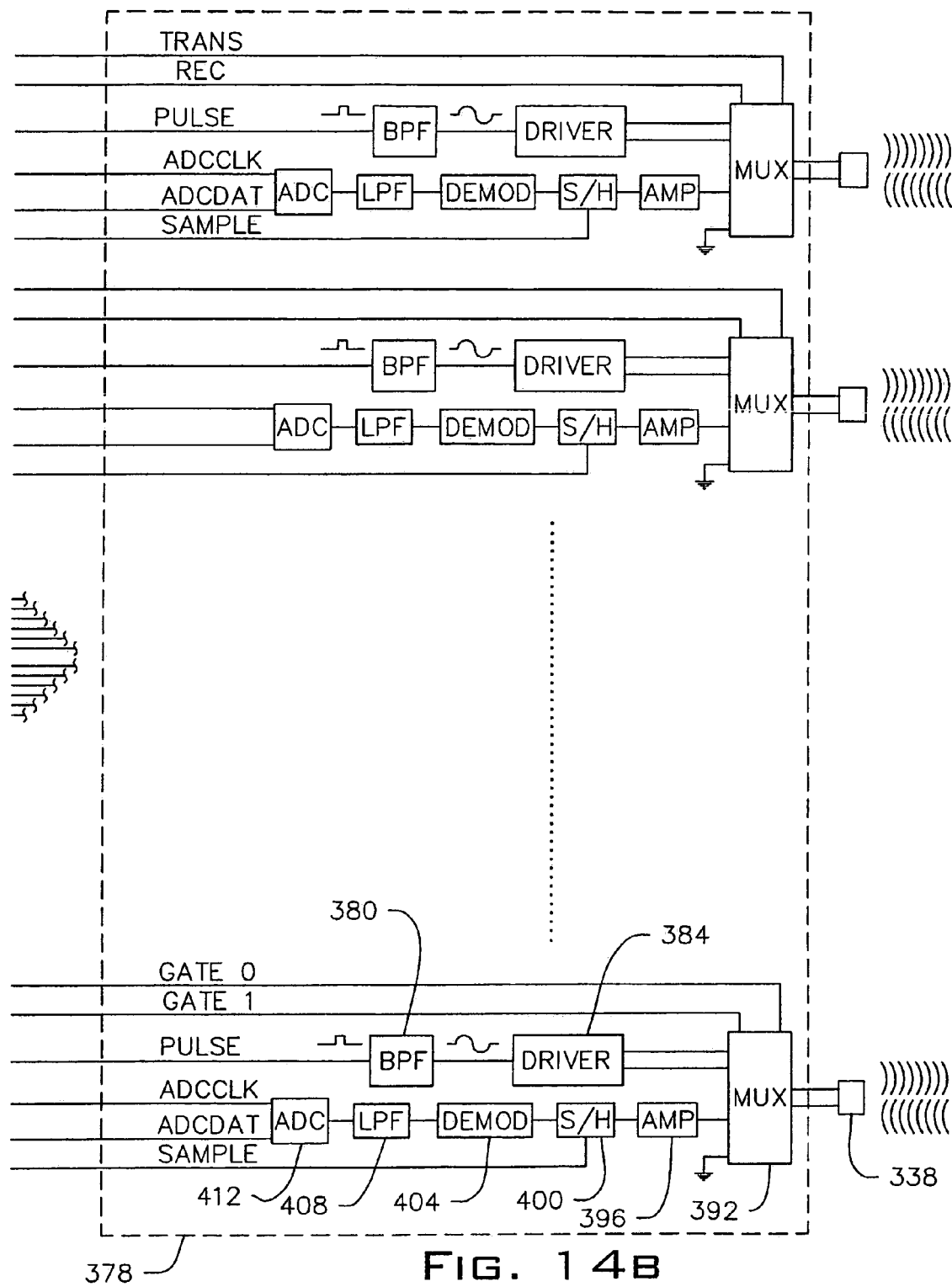

For example, as shown in FIG. 12b, each of the transceivers 338 has a 0.75 inch diameter and a proportional band area of 0.25 inches as defined by a start point 363 and an end point 364. Because the disposition of the transceivers 338 is repetitive, for purposes of clarity, the disposition of only four transceivers 338a, 338b, 338c, and 338d will be discussed in further detail. An end point 364a of the proportional band area of transceiver 338a is aligned with a start point 363b of the proportional band area of transceiver 338b so as to overlap by 0.025 inches along the length 360 of the transceiver block 326. An end point 364b of the proportional band area of transceiver 338b is aligned with a start point 363c of the proportional band area of transceiver 338c so as to overlap by 0.025 inches along the length 360 of the transceiver block 326. An end point 364c of the proportional band area of transceiver 338c is aligned with a start point 363d of a proportional band area of transceivers 338d so as to overlap by 0.025 inches along the length 360 of the transceiver block 326.

Therefore, it can be seen that the alignment and overlap of the plurality of transceivers 338 along the length 360 of the at least one transceiver block 326 essentially reduces gaps along the length of the at least one transceiver block 326. Although the transceivers 338 are discussed herein as being arranged so as to reduce gaps along the length 360 of the at least one transceiver block 326, it should also be understood that the same method of alignment of the transceivers 338 can be applied along the width 362 of the at least one transceiver block 326. Also, because of real-world client requests to reduce the number of transceivers 338 (e.g. to reduce costs), the present invention contemplates that not all gaps along the length 360 and/or width 362 of the at least one transceiver block 326 have to be reduced when disposing the transceivers 338 in the staggered matrix formation. Further, the present invention contemplates that at least some of the start points 363 and end points 364 of the proportional band areas may be aligned such that the proportional band areas are spaced a minimal distance apart rather than being overlapped.

Therefore, it can be seen that in general the number of transceivers 338 in each row and the number of rows of transceivers 338 in the staggered matrix formation of the at least one transceiver block 326 can depend on various considerations, such as the intended application of the sensor system 300, the dimensions of the at least one web material 14 or portions thereof being sensed, the dimensions of each of the transceivers 338, allowance for gaps in the transceiver block 326, the desired dimensions of the sensor field of view 346, the number of transceiver blocks 326 included in the sensor system 10, costs, etc.

As best shown in FIG. 11, the sensor system 300 also includes a master unit 334, which communicates with the at least one transceiver block 326 to control the plurality of transceivers 338. The master unit 334 controls the operation of each of the transceivers 338 so as to control whether each of the transceivers 338 acts as a transmitter and generates ultrasonic signals, or as a receiver and receives ultrasonic signals. In one embodiment, to control the operation of the transceivers 338, the transceivers 338 are multiplexed between a transmitter function, a receiver function, and ground (i.e. an off state).

In a similar manner as the transmitters 38 discussed with respect to the sensor system 10, to cause the transceivers 338 of sensor system 300 to generate ultrasonic signals, the master unit 334 periodically transmits to each of the transceivers 338 of the at least one transceiver block 326 a transmitter drive signal to selectively cause the transceivers 338 to "fire" or transmit periodic ultrasonic signals. In one embodiment, when the transceivers 333 are not transmitting ultrasonic signals, to reduce undesired reception and noise by each of the transceivers 338, the master unit 334 also selectively outputs receiver cutoff signals to each of the transceivers 338 so as to selectively toggle the transceiver 338 in between a first mode wherein the transceiver 338 is "on" and permitted to form the receiver output signal responsive to the transceiver 338 sensing ultrasonic signals, and a second mode wherein the transceiver 338 is "off" and restricted from providing the receiver output signal (in a similar manner to the receivers 42 discussed with respect to the sensor system 10).

To minimize interference between transceivers 338, the master unit 334 can further control the firing sequence and/or frequency of the transceivers 338 so that each transceiver 338 (or group of transceivers 338) transmits ultrasonic signals at a different time and/or frequency than adjacently disposed transceivers 338 (or groups of transceivers 338), and receives ultrasonic signals at a different time than adjacently disposed transceivers 338 (or groups of transceivers 338). For example, the master unit 334 can synchronize the transmitter drive signals sent to two or more transceivers 338 of the at least one transceiver block 326. Also, the master unit 34 can synchronize the receiver cutoff signals sent to two or more transceivers 338. Further, when the sensor system 300 includes more than one transceiver block 326, the master unit 334 can synchronize the transmitter drive signals and/or the receiver cutoff signals outputted to the transceiver blocks 326. The master unit 334 may also be adapted to send and receive diagnostic data from each of the transceivers 338 of the at least one transceiver block 326.

The master unit 334 also receives the receiver output signals generated by the plurality of transceivers 337. In one embodiment, in a manner similar to the master unit 34 of the sensor system 10, the master unit 334 of the sensor system 300 utilizes the receiver output signals outputted by the plurality of transceivers 338 to generate sensor output signals indicative of the position of at least one edge 12 of the at least one web material 14 by setting a threshold value to which the receiver output signals are compared. The threshold value is generally set such that when each receiver output signal from each transceiver 338 is compared to the threshold value, the comparison indicates whether at least a portion of the ultrasonic signals generated by the transceiver 338 was interfered with and thus not received by the transceiver 338. As such, the comparison of the output receiver signals of the transceivers 338 and the threshold value can be utilized by the master unit 334 to determine the position of at least one edge 12 of the at least one web material 14 within the sensor field of view 346. Also, other information can be determined therefrom, such as the center position of the at least one web material 14 and transitions between two or more web materials 14.

In another embodiment, in a manner similar to the master unit 34 of the sensor system 10, the master unit 334 of the sensor system 300 utilizes the receiver output signals outputted by the transceivers 338 to generate sensor output signals indicative of the position of at least one edge 12 of the at least one web material 14 by comparing the receiver output signals relative to each other. By comparing the receiver output signals, the master unit 334 can determine the relative amount of ultrasonic signals that were received by each transceiver 338. As such, the relative comparison of the output receiver signals can be utilized by the master unit 334 to determine the position of at least one edge 12 of the at least one web material 14 within the sensor field of view 346 by evaluating transitions between receiver output signal values. Also, other information can be determined therefrom, such as the center position of the at least one web material 14 and transitions between two or more web materials 14.

By comparing the receiver output signals to a threshold value, or by comparing the receiver output signals relative to each other, the master unit 334 can determine the position of at least one edge 12 of the at least one web material 14, a width 15 of the at least one web material 14, a transition between two or more web materials 14, or combinations thereof, and generate at least one sensor output signal indicative of the same. For example, the master unit 334 may generate a sensor output signal indicative of the position of a first edge 12a of the at least one web material 14. In another example, the master unit 334 may output two sensor output signals, wherein one sensor output signal is indicative of the first edge 12a of the at least one web material 14, and the other sensor output signal is indicative of another edge 12b of the at least one web material 14. Further, the master unit 334 can output a sensor output signal indicative of the width 15 of the at least one web material 14 by determining the distance between the two edges 12a and 12b of the at least one web material 14. In another example, such as shown in FIG. 10b, when two web materials 14a and 14b are being sensed by the sensor system 10, the master unit 334 can use the receiver output signals to determine the position of an edge 12aa of the first web material 14a. The master unit 334 can also compare the receiver output signals to detect a relative transition in the receive output signals so as to determine the position of an edge 12ab of the second web material 14b, and thereby determine a transition between the two web materials 14a and 14b.

Similar to the master unit 34 of the sensor system 10, the at least one sensor output signal can be outputted by the master unit 334 of the sensor system 300 to other devices (not shown), such as a for example a conventional web guiding signal processor or computer, which may be in communication with the sensor system 300. The sensor system 10 can also be connected to a serial bus for a wider range of applications.

Figure 13:
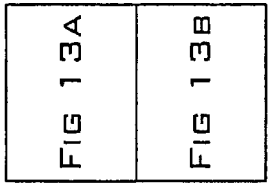
FIG. 13 is a block diagram of one embodiment of a master unit of the sensor system.

Referring now to FIG. 13, shown therein is one embodiment of the master unit 334 of the sensor system 300, which is similar to the master unit 34 of the system 10 shown in FIG. 5. Thus, for purposes of clarity, the master unit 334 will be summarily discussed herein. The master unit 334 includes a controller 367 and a control circuit 368. The controller 367 cooperates with the control circuit 368 so that the master unit 334 selectively outputs transmitter drive signals and receiver cutoff signals to the plurality of transceivers 338, and selectively receives receiver output signals outputted by the plurality of transceivers 338 of the at least one transceiver block 326.

In one embodiment, the controller 367 of the master unit 334 is a microcontroller, such as for example a microcontroller with an ARM9 microprocessor core. The control circuit 368 of the master unit 34 is a complex programmable logic device (CPLD) or field-programmable gate array (FPGA), which includes data registers for adder-corrected clock synchronization. Preferably, the control circuit 368 of the master unit 334 further includes a master clock for synchronization purposes (as discussed further below).

The master unit 334 may further include a plurality of network interfaces 369, such as for example a bidirectional bus or ethernet connection, so as to be in communication with a network area. For example, when the sensor system 300 includes more than one transceiver block 326, the master unit 334 can synchronize the transmitter drive signals and/or the receiver cutoff signals outputted to each transceiver block 326 via one of the network interfaces 369 so as to minimize interference between the transceiver blocks 326.

The master unit 334 can also include a temperature compensation circuit 370 for sensing and compensating for environmental temperature. Similar to the compensation circuit 70 of sensor system 10, in one embodiment the temperature compensation circuit 370 of sensor system 300 includes at least one temperature sensor 371 and an analog-to-digital converter 372. The temperature sensor 371 generates a temperature signal indicative of the absolute temperature surrounding the sensor system 300, which is outputted to the master unit 334 via the analog-to-digital converter 372. The master unit 334 receives the receiver output signals from the transceiver block 326 and the temperature signal from the temperature sensor 371. In response thereto, the master unit 34 utilizes at least one of a plurality of stored temperature compensation values to generate sensor output signals which more accurately indicate the position of the of the at least one web material 14. While the temperature compensation circuit 370 has been described as being included in the master unit 334, it should be understood that the temperature compensation circuit 370 (or the at least one temperature sensor 371) may be included in the transceiver block 326, especially if significant temperature gradients may be expected over the sensor field of view 346.

The master unit 334 may further include an analog output circuit 373 for outputting the sensor output signals to other devices, such as a for example a conventional web guiding signal processor or computer (not shown), which may be in communication with the sensor system 300. In one embodiment, the analog output circuit 373 includes a first E/I converter 374, a second E/I converter 375, a third E/I converter 376, and a digital-to-analog converter 377. The master unit 334 outputs a signal which is indicative of the location of the first edge 12a of the web material 14 to the first E/I converter 374 via the digital-to-analog converter 377. The master unit 334 outputs a signal which is indicative of the location of the second edge 12b of the web material 14 to the second E/I converter 375 via the digital-to-analog converter 377. Similarly, the master unit 334 outputs a signal which is indicative of the width 15 of the at least one web material 14 to the third E/I converter 376 via the digital-to-analog converter 377.

The first E/I converter 374 outputs an enhanced sensor output signal indicative of the first edge 12a so that such sensor output signal can be received by the conventional web guiding signal processor. The second E/I converter 375 outputs an enhanced sensor output signal indicative of the second edge 12b so that such sensor output signal can be received by the conventional web guiding signal processor. The third E/I converter 376 outputs an enhanced signal indicative of the web width 15 so that such signal can be received by the conventional web guiding signal processor. That is, in a manner similar to the E/I converters 74, 75, and 76 of the master unit 34 of the sensor system 10, the E/I converters 374, 375, and 376 of the master unit 334 of the sensor system 334 convert the analog signals received from the digital-to-analog converter 377 and output current signals. These signals can be voltage-to-current converted signals having a range of between 0-20 milliamperes.

While the signals output by the analog output circuit 373 are described as being outputted as current signals, it should be understood that the output signals from the master unit 334 may be converted into any desirable format required by a particular web guide control system.

Figure 14:
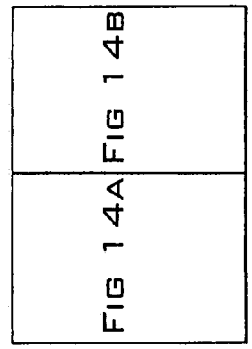
FIG. 14 is a block diagram of one embodiment of a transceiver block of the sensor system.

Referring now to FIG. 14, shown therein in block diagram form is one embodiment of one transceiver block 326 constructed in accordance with the present invention. The transceiver block 326 includes the plurality of transceivers 338 (only one being labeled for purposes of clarity), wherein each transceiver 338 is selectively capable of generating ultrasonic signals in response to the transmitter drive signal outputted by the master unit 334 to the transceiver 338, and receiving ultrasonic signals in response to the receiver cutoff signal outputted by the master unit 334 to the transceiver 338. Although the transceiver block 326 is shown in FIG. 14 as including seven transceivers 338, it should be understood that the transceiver block 326 can have any number of transceivers 338.

In one preferred embodiment, the transceiver block 326 further includes a transmit/receive circuit 378 and a data transmission circuit 379 to exchange data between the master unit 334 and the plurality of transceivers 338. In general, the transmit circuit 378 and data transmission circuit 379 cooperate with the master unit 334 to set and synchronize timing patterns for the transceivers 338, to fire the transceivers 338, to toggle on and off the transceivers 338, to receive the receiver output signals from the transceivers 338, and to identify or diagnose the transceivers 338 of the at least one transceiver block 326. More particularly, the data transmission circuit 379, which can be for example a complex programmable logic device (CPLD), cooperates with the master unit 334 to control which transceiver 338 (or group of transceivers 338) receives the transmitter drive signal and receiver cutoff signals. The transmit/receive circuit 378 of the transceiver block 326 of the sensor system 300 essentially performs the combined functions of the transmit circuit 78 of the transmitter block 26 and the receive circuit 88 of the receiver block 30 discussed with respect to the sensor system 10. The transmit/receive circuit 378 of the transceiver block 326 of the sensor system 300 conditions the transmitter drive signal before the transmitter drive signal is used to drive the selected transceiver 338 (or group of transceivers 338), toggles the selected transceiver 338 (or group of transceivers 338) in response to the receiver cutoff signal outputted by the master unit 334 via the data transmission circuit 379, and smooths and amplifies the receiver output signals generated by the selected transceiver 338 (or group of transceivers 338).

The master unit 334 selectively outputs transmitter drive signals to the data transmission circuit 379 of the transceiver block 326 via a serial bus, such as for example a bidirectional RS-485. In general, the transmitter drive signal is representative of substantially one cycle of a substantially sinusoidally shaped waveform. In one embodiment, the transmitter drive signal has a preselected frequency of about 220 kHz, and the period at which the master unit 334 transmits the transmitter drive signal is about 5 milliseconds. The transmitter drive signals are received by the data transmission circuit 379 which selectively passes the transmitter drive signals to the transmit/receive circuit 378 to fire selected transceivers 338 and cause the selected transceivers 338 to transmit ultrasonic signals.

The master unit 334 also selectively outputs receiver cutoff signals to the data transmission circuit 379 via the serial bus. The receiver cutoff signals are received by the data transmission circuit 379 which selectively passes the receiver cutoff signals to the transmit/receive circuit 378 to toggle the selected transceivers 338 when the selected transceivers are not transmitting ultrasonic signals. The master unit 334 also receives the receiver output signals generated by the selected transceivers 338 via the transmit/receive circuit 378 and data transmission circuit 379.

Preferably, the data transmission circuit 379 communicates with the transmit/receive circuit 378 via a plurality of signal paths so that the transmitter drive signals and receiver cutoff signals can be outputted via the transmit/receive circuit 378 to at least one selected transceiver 338 (or group of transceivers 338), and so that the receiver output signals can be outputted from each transceiver 338 to the data transmission circuit 379.

Similar to the transmit circuit 78 of the at least one transmitter block 26 of the sensor system 10, in one preferred embodiment, as shown for example in FIG. 14, the transmit/receive circuit 378 of the at least one transceiver block 326 of the sensor system 300 includes a combination of one bandpass filter 380 (only one being labeled for purposes of clarity) and one driver 384 (only one being labeled for purposes of clarity) for each of the transceivers 338 of the transceiver block 326, so that each transceiver 338 can be controlled independently of the other transceivers 338. In such an embodiment, the bandpass filters 380 are identical and the drivers 384 are identical if the transceivers 338 operate at the same frequency. However, if the transceivers 338 operate at different frequencies, the bandpass filters 380 will be different. Also, it should be apparent to one skilled in the art that similar to the transmitters 38 of the at least one transmitter block 26 of the sensor system 10 discussed above, if more than one transceiver 338 of the at least one transceiver block 326 of the sensor system 300 operates at the same frequency and are activated at the same time, then the transceivers 338 can also share common components in the transmit/receive circuit 378 to reduce costs and real estate requirements.

Because each transceiver 338 and corresponding bandpass filter 380 and driver 384 operates in a similar manner, for purposes of clarity, only the operation of one transceiver 338 and corresponding bandpass filter 80 and driver 84 is discussed in further detail below.

The bandpass filter 380 is tuned to pass substantially only the selected frequency of the transmitter drive signal and to block substantially all other frequencies, including harmonic frequencies and noise which may result from the transmission of the transmitter drive signal or the noise from a 60-Hz supply voltage, for example. When the master unit 334 controls the transceiver 338 to generate ultrasonic signals, the bandpass filter 380 receives the periodic transmitter drive signal from the master unit 334 via the data transmission circuit 379, and in response thereto, the bandpass filter 380 conditions the transmitter drive signal to drive the transceiver 338. The conditioned transmitter drive signal will be a substantially sinusoidal waveform. The bandpass filter 380 outputs the conditioned transmitter drive signal to the driver 384. In response thereto, the driver 384 drives the transceiver 338 so as to cause the transceiver 338 to generate ultrasonic signals for the duration of the transmitter drive signal. The at least one driver 384 may be push-pull or single ended with the other terminal of the transceiver 338 connected to ground.

In one preferred embodiment, as shown for example in FIG. 14, the transmit/receive circuit 378 of the transceiver block 326 further includes a combination of one multiplexer 392, one amplifier 396, one sample and hold 400, one demodulator 404, one lowpass filter 408, and one analog-to-digital converter 412 (only one of each being labeled for purposes of clarity) for each of the transceivers 338 of the transceiver block 326. However, it should be apparent to one skilled in the art that similar to the receivers 42 of the at least one receiver block 30 of the sensor system 10 discussed above, if more than one transceiver 338 of the at least one transceiver block 326 of the sensor system 300 operates at the same frequency and/or are activated at the same time, then the transceivers 338 can also share common components and/or multiple multiplexers 392 can be used in the transmit/receive circuit 378 to reduce costs and real estate requirements.

Because each transceiver 338 and corresponding multiplexer 392, amplifier 396, sample and hold 400, demodulator 404, lowpass filter 408, and analog-to-digital converter 412 operates in a similar manner, for purposes of clarity, only the operation of one transceiver 338 and corresponding multiplexer 392, amplifier 396, sample and hold 400, demodulator 404, lowpass filter 408, and analog-to-digital converter 412 is discussed in further detail below.

To toggle the transceiver 338 on and allow the transceiver 338 to receive ultrasonic signals and generate receiver output signals in response thereto, the receiver cutoff signal is outputted by the master unit 334 and passed by the data transmission circuit 379 to the transmit/receive circuit 378. The corresponding multiplexer 392 of the transmit/receive circuit 378 toggles the transceiver 338 so that the transceiver 338 is permitted to receive ultrasonic signals for the duration of the receive cutoff signal outputted by the master unit 334. In one embodiment, to toggle the transceiver 338, the multiplexer 392 selectively clamps the positive and negative terminals of the transceiver 338 to ground. For example, the transceiver 338 can be turned "off" by the receiver cutoff signal in the second mode by clamping the positive terminal of the transceiver 338 to ground.

By toggling the transceiver 338 between the first mode and the second mode when the transceiver 338 is not transmitting ultrasonic signals, the transceiver 338 is only permitted to generate the receiver output signals during each period for the predetermined time after the transmitter drive signal has been transmitted to the transceiver 338 and the transceiver has generated ultrasonic signals in response thereto. The receiver cutoff signal is generally sent to the transceiver 338 in sequence and in synchronization with the transmitter drive signal sent to the transceiver 338, taking into account the time needed for the transceiver 338 to generate the ultrasonic signals and for the ultrasonic signals to travel the sensing gap 358 of the sensor field of view 346, be reflected by the reflective material 342 of the at least one reflector 330, and travel back to the transceiver 338. Thus it can be seen that the predetermined time that the transceiver 338 is permitted to generate the receiver output signal will be determined by: (1) the frequency of the transmitter drive signal; and (2) the sensing gap 358 of the of the sensor field of view 346. Given a transmitter drive signal of about 220 kHz, and a sensing gap 358 of about one inch, a predetermined time period between about 200 microseconds to about 400 microseconds has been found to be appropriate, depending on the amount of time that passes between the start of the transmitter drive signal and the start of the receiver cutoff signal. By synchronizing the transmitter drive signal and the receiver cutoff signal, interference between different transceivers 338 as well as other undesired noise can be reduced.

When the transceiver 338 is toggled on and receives ultrasonic signals, the transceiver 338 generates a receiver output signal indicative of the ultrasonic signals received, which is outputted to the multiplexer 392. The multiplexer 392 passes the receiver output signal received to the amplifier 396 which amplifies the receiver output signal. The amplified receiver output signal is passed to the sample and hold 400. The sample and hold 400 acts as a spike remover which removes all voltage spikes from the amplified receiver output signal. The stripped, amplified receiver output signal is then passed to the demodulator 404. The demodulated receiver output signal is passed by the demodulator 404 to the lowpass filter 408, which smooths the receiver output signal. The filtered receiver output signal is then passed to the analog-to-digital converter 412 so as to form a DC signal which is outputted to the master unit 334 via the data transmission circuit 379 so that the receiver output signal can be utilized by the master unit 334 to generate the sensor output signals (as discussed above).

In one embodiment, the data transmission circuit 379 preferably has dedicated hardware logic that are adapted for time-critical functions such as gating and controlling the sample-and-holds 400, which are generally synchronized to the firing of the corresponding transceiver 338. The data transmission circuit 379 is synchronized utilizing the master clock of control circuit 368 of the master unit 334. Further, the transceiver block 326 can include a microcontroller (not shown) which cooperates with the data transmission circuit 379 to handle data communications, to control the analog-to-digital converters 412, or to perform data acquisitions via on-chip analog-to-digital functions.

As discussed above, in one embodiment of the present invention, the master unit 334 controls the firing and reception sequence and/or frequency of the transceivers 338 so that each transceiver 338 (or group of transceivers 338) transmits ultrasonic signals at a different time and/or frequency than adjacently disposed transceivers 338 (or groups of transceivers 338), and receives ultrasonic signals at a different time than adjacently disposed transceivers 338 (or groups of transceivers 338). The timing pattern in which each of the plurality of transceivers 338 is "fired", i.e. caused to transmit ultrasonic signals, and toggled "on", i.e. permitted to generate receiver output signals responsive to the transceiver 338 receiving ultrasonic signals, will depend on the relative physical arrangement of the transceivers 338. Also, the distance between each transceiver 338 and the reflective material 342 of the corresponding reflector 330 will also affect signal travel timing relationships and therefore may require different firing and reception timing patterns. In a manner similar to the firing and reception patterns discussed above with respect to the sensor system 10, the firing and reception patterns of the sensor system 300 utilizes the master clock of the control circuit 368 of the master unit 334. Also, similar to sensor system 10, such synchronization for the sensor system 300 can be implemented using IEEE 1588 Precision Time Protocol techniques.

In a similar manner discussed with the transmitters 38 and receivers 42 of the sensor system 10, the transceivers 338 of the sensor system 300, which are located within a predetermined range of the position of the at least one edge 12 of the at least one web material 14, can be selectively actuated and deactuated so as to reduce power consumption and processing capacity of the sensor system 300, and provide logical web edge sensing.

From the above description it is clear that the present invention is well adapted to carry out the objects and to attain the advantages mentioned herein as well as those inherent in the invention. While more specific embodiments of the invention has been described for purposes of this disclosure, it will be understood that numerous changes may be made which will readily suggest themselves to those skilled in the art and which are accomplished within the spirit of the invention disclosed and defined in the appended claims.

What is claimed is:

1. A sensor system for determining the position of at least one edge of at least one web material traveling along a predetermined travel path, the sensor system comprising:

at least one transceiver block disposed substantially adjacent the travel path, the at least one transceiver block having a plurality of transceivers, each transceiver being capable of selectively transmitting ultrasonic signals upon receipt of a transmitter drive signal so as to transmit ultrasonic signals across at least a portion of the travel path;

at least one reflector spaced a distance from the at least one transceiver block whereby the travel path passes in between the at least one transceiver block and the at least one reflector, the at least one reflector having a reflective material positioned so as to reflect at least a portion of the ultrasonic signals transmitted by the at least one transceiver block back to the transceiver block;

a master unit selectively toggling at least one of the transceivers between a first mode for generating an ultrasonic signal, a second mode for forming a receiver output signal upon receipt of an ultrasonic signal, and a third mode for electronically dampening and thereby disabling the at least one of the transceivers, and means for generating at least one sensor output signal based on the receiver output signal, wherein the sensor output signal is indicative of the position of the least one edge of the at least one web material.

2. The sensor system of claim 1, further comprising a means for selectively actuating the transceivers within a predetermined range of the at least one edge of the at least one web material.

3. The sensor system of claim 1, further comprising means for determining a transition between two or more web materials.

4. The sensor system of claim 1, wherein each transceiver of the at least one transceiver block is positioned in a staggered formation to prevent formation of gaps in the ultrasonic signals transmitted between the reflector and the transceiver block.

5. The sensor system of claim 1, wherein the master unit controls a reception sequence of the transceivers so that each transceiver or group of transceivers receives ultrasonic signals at a different time than adjacently disposed transceivers or groups of transceivers.

6. The sensor system of claim 1, wherein the at least one of the transceivers is selectively toggled from the third mode to the first mode in synchronization with the transmission of the transmitter drive signal to the at least one of the transceivers.

7. The sensor system of claim 1, wherein each transceiver of the at least one transceiver block transmits ultrasonic signals at a different time than an adjacently disposed transceiver.

8. The sensor system of claim 1, wherein a predetermined group of transceivers of the at least one transceiver block transmits ultrasonic signals at a different time than an adjacently disposed predetermined group of transceivers.

9. The sensor system of claim 1, wherein each transceiver of the at least one transceiver block transmits ultrasonic signals at a different frequency than an adjacently disposed transceiver.

10. The sensor system of claim 1, wherein a predetermined group of transceivers of the at least one transmitter block transmits ultrasonic signals at a different frequency than an adjacently disposed predetermined group of transceivers.

11. The sensor system of claim 1, further comprising a means for sensing an environmental temperature surrounding at least a portion of the sensor system, and for enhancing the receiver output signals with at least one stored temperature compensation value so as to generate a sensor output signal in which changes in the environmental temperature no longer have a substantial effect on the nature of the sensor output signal.

12. A sensor system for determining the position of at least one edge of at least one web material traveling along a predetermined travel path, the sensor system comprising:

at least one transceiver block disposed substantially adjacent the travel path, the at least one transceiver block having a plurality of transceivers, each transceiver being capable of selectively transmitting ultrasonic signals upon receipt of a transmitter drive signal so as to transmit ultrasonic signals across at least a portion of the travel path;

at least one reflector spaced a distance from the at least one transceiver block whereby the travel path passes in between the at least one transceiver block and the at least one reflector, the at least one reflector having a reflective material positioned so as to reflect at least a portion of the ultrasonic signals transmitted by the transceivers of the at least one transceiver block substantially back to the transceivers;

wherein the transceivers of the at least one transceiver block are further capable of receiving ultrasonic signals and generating receiver output signals responsive to the transceivers sensing ultrasonic signals;

means for periodically transmitting to each transceiver of the at least one transceiver block a transmitter drive signal to cause said each transceiver to transmit ultrasonic signals at a different time than an adjacently disposed transceiver;

means for selectively toggling said each transceiver of the at least one transceiver block when said each transceiver is not transmitting ultrasonic signals, wherein said each transceiver is toggled in between a first mode wherein said each transceiver is permitted to form the receiver output signals responsive to said each transceiver sensing ultrasonic signals, and a second mode wherein said each transceiver is restricted from providing the receiver output signals, wherein said each transceiver is toggled from the second mode to the first mode to permit said each transceiver to receive the ultrasonic signals generated by said each transceiver in synchronization with the transmission of the transmitter drive signal to said each transceiver, and then said each transceiver is automatically toggled back to the first mode after a predetermined time so as to eliminate any noise in the receiver output signals; and means for receiving receiver output signals from the plurality of transceivers of the at least one transceiver block and utilizing the receiver output signals to determine the position of at least one edge of the at least one web material as the at least one web material travels along the travel path.

* * * * *

UNITED STATES PATENT AND TRADEMARK OFFICE
CERTIFICATE OF CORRECTION

PATENT NO. : 7,357,027 B2
APPLICATION NO. : 11/483203
DATED : April 15, 2008
INVENTOR(S) : Md M. Haque et al.

It is certified that error appears in the above-identified patent and that said Letters Patent is hereby corrected as shown below:

Column 3, line 61: Before "output" delete "receive" and replace with -- receiver --.
Column 14, line 21: After "each" delete "transmit" and replace with -- transmitter --.

Signed and Sealed this

Eighth Day of July, 2008

JON W. DUDAS
*Director of the United States Patent and Trademark Office*